(12) United States Patent
Zhong et al.

(10) Patent No.: US 9,695,175 B2
(45) Date of Patent: Jul. 4, 2017

(54) HIGHLY SELECTIVE C-MET INHIBITORS AS ANTICANCER AGENTS

(71) Applicant: Crown Bioscience Inc. (Taiwan), Taipei (TW)

(72) Inventors: Boyu Zhong, Taicang (CN); Chuan Shih, Taicang (CN); Hongbin Yuan, Taicang (CN); Feng Zhou, Taicang (CN)

(73) Assignee: CB THERAPEUTICS INC., Grand Cayman (KY)

( * ) Notice: Subject to any disclaimer, the term of this patent is extended or adjusted under 35 U.S.C. 154(b) by 0 days.

(21) Appl. No.: 14/424,395

(22) PCT Filed: Aug. 1, 2013

(86) PCT No.: PCT/CN2013/080598
§ 371 (c)(1),
(2) Date: Feb. 26, 2015

(87) PCT Pub. No.: WO2014/032498
PCT Pub. Date: Mar. 6, 2014

(65) Prior Publication Data
US 2015/0218171 A1    Aug. 6, 2015

(30) Foreign Application Priority Data
Sep. 3, 2012 (CN) .......................... 2012 1 0322359

(51) Int. Cl.
| | | |
|---|---|---|
| C07D 487/04 | (2006.01) | |
| C07D 471/04 | (2006.01) | |
| C07D 513/04 | (2006.01) | |

(52) U.S. Cl.
CPC ......... *C07D 487/04* (2013.01); *C07D 471/04* (2013.01); *C07D 513/04* (2013.01)

(58) Field of Classification Search
None
See application file for complete search history.

(56) References Cited

FOREIGN PATENT DOCUMENTS

| | | |
|---|---|---|
| JP | 2009-525263 A | 7/2009 |
| JP | 2009-543789 A | 12/2009 |
| WO | 2007/075567 A1 | 7/2007 |
| WO | 2008/051805 A2 | 5/2008 |
| WO | 2012/015677 A1 | 2/2012 |

OTHER PUBLICATIONS

International Search Report for International Application No. PCT/CN2013/080598 dated Nov. 7, 2013, 6 pages.

*Primary Examiner* — Heidi Reese
(74) *Attorney, Agent, or Firm* — Jun He Law Offices P.C.; James J. Zhu

(57) ABSTRACT

Disclosed are novel nitrogen-containing, heterocyclic, c-Met inhibitor compounds, processes for their preparation and formulations thereof. The compounds are useful as therapeutical agents for the inhibition, regulation, and control of c-Met kinase signal pathway, and useful for treating in a subject a cell proliferative disorder or disorders mediated by c-Met.

35 Claims, No Drawings

HIGHLY SELECTIVE C-MET INHIBITORS AS ANTICANCER AGENTS

FIELD OF THE INVENTION

The present invention relates to novel nitrogen-containing, heterocyclic, c-Met inhibitors, processes for their preparation, formulations thereof, their use as therapeutical agents for the inhibition, regulation, and control of c-Met kinase signal pathway, and their use for treating in a subject a cell proliferative disorder or disorders mediated by c-Met.

BACKGROUND

Hepatocyte growth factor (HGF) (also referred to as the scatter factor) receptor c-Met is to regulate cell proliferation, morphogenesis, and motility receptor tyrosine kinase. The c-Met gene is translated into 170 kD protein, which is processed to a 140 kD transmembrane subunit and a 50 kD sugar-conjugated extracellular a subunit together as the cell surface receptor.

In various human solid tumors, the normal cells change by c-Met mutations, the overexpression of c-Met and/or of HGF/SF, or both. It is considered to participate in angiogenesis, tumor progression, invasion, and metastasis. For an example, the cell lines with uncontrolled c-Met activity cell line is highly invasive and metastasis. A significant difference between a normal cells and a changed expressing c-Met receptor cell is in that the phosphorylation of the tyrosine kinase domain is independent of the ligand in tumor cells.

c-Met mutation/replacement have already been identified in tumor and cancer diseases including papillary renal cancer, breast cancer, rectal colon cancer, gastric cancer, neural glioma cancer, ovarian cancer, hepatocellular carcinoma, head and carotid squamous cells cancer, testicular cancer, basal cell carcinoma, hepatocellular carcinoma, sarcoma, malignant pleural mesothelioma, melanoma, multiple myeloma, osteosarcoma, pancreatic cancer, prostate cancer, synovial sarcoma, thyroid cancer, non-small cell lung cancer (NSCLC) bladder transitional cell carcinoma and small cell lung cancer, testicular cancer, basal cell carcinoma, liver cancer—leukemia, lymphoma and myeloma—for example, acute lymphoblastic leukemia (ALL), acute myeloid leukemia (AML), acute promyelocytic tabletsleukemia (APL), chronic lymphocytic leukemia (CLL), chronic myelogenous leukemia (CML), chronic neutrophilic leukemia (CNL), acute undifferentiated leukemia (AUL), anaplastic large cell lymphoma (ALCLmyelodysplastic), prolymphocytic leukemia (PML), childhood Reap—monocytic leukemia (JMML), adult T-cell ALL, accompanied by a three-line myelodysplastic AML (AML/TMDS), mixed lineage leukemia (MLL) syndrome (MDSs), myeloproliferative diseases (MPD), multiple myeloma (MM), bone marrow sarcoma, non-Hodgkin's lymphoma and Hodgkin's disease (also known as Hodgkin's lymphoma).

WO2012/015677 to Eli Lilly and Company discloses 6-(1-methyl-1H-pyrazol-4-yl)-3-(2-methy-2H-indazol-5-yl-thio)-[1,2,4]triazolo[4,3-b]pyridazine c-Met inhibitors, useful in treating cancer mediated by activity of c-Met receptors. WO2009/106577 to Novartis Pharma discloses imidazo[1,2-b]pyridazine derivatives for the treatment of a human or animal body with respect to a proliferative disease, in particular a c-Met tyrosine kinase mediated disease; their use for manufacturing a medicament for the treatment of such diseases; pharmaceutical compositions comprising these compounds, optionally in the presence of a combination partner; and processes for their preparation.

WO2007/075567 to Janssen Pharmaceutica discloses triazolopyridazine compounds, the use of such compounds as protein tyrosine kinase modulators, particularly inhibitors of c-Met, the use of such compounds to reduce or inhibit kinase activity of c-Met in a cell or a subject and modulate c-Met expression in a cell or subject, and the use of such compounds for preventing or treating in a subject a cell proliferative disorder and/or disorders related to c-Met. WO2007/075567 is further directed to pharmaceutical compositions comprising these compounds and to methods for treating conditions such as cancers and other cell proliferative disorders.

WO2008/051805 to SGX Pharmaceuticals discloses triazolopyridazine protein kinase modulators and methods of using these compounds to treat diseases mediated by kinase activity. In particular, the compounds of the present disclosure may be used to modulate and/or inhibit tyrosine kinases, including Met. Further, the compounds may be used to reduce or inhibit kinase activity of Met in a cell or subject, and to modulate Met expression in a cell or subject. The disclosed compounds are also useful for preventing or treating in a subject a cell proliferative disorder and/or disorders related to Met.

This present invention provides novel, highly-selective, nitrogen-containing, heterocyclic, c-Met inhibitors that exhibit improved anticancer activity over known compounds.

SUMMARY OF THE INVENTION

In one aspect, the invention provides compounds of Formula I

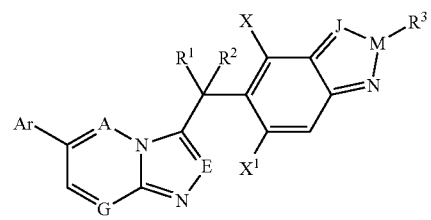

wherein:
$R^1$ and $R^2$ are independently hydrogen or halogen;
X and $X^1$ are independently hydrogen or halogen;
A and G are independently CH or N, or CH=G is replaced with a sulfur atom;
E is N;
J is CH, S or NH;
M is N or C;
Ar is aryl or heteroaryl, optionally substituted with 1-3 substituents independent selected from: $C_{1-6}$alkyl, $C_{1-6}$alkoxyl, halo-$C_{1-6}$alkyl, halo-$C_{1-6}$ alkoxy, $C_{3-7}$cycloalkyl, halogen, cyano, amino, —$CONR^4R^5$, —$NHCOR^6$, —$SO_2NR^7R^8$, $C_{1-6}$alkoxyl-$C_{1-6}$alkyl-, amino-$C_{1-6}$alkyl-, heterocyclyl and heterocyclylalkyl, or two connected substituents together with the atoms to which they are attached form a 4-6 membered lactam fused with the aryl or heteroaryl;
$R^3$ is hydrogen, $C_{1-6}$alkyl, $C_{1-6}$alkoxy, halo$C_{1-4}$ alkyl, halogen, amino, or —CONH—$C_{1-6}$ alkyl-heterocyclyl;
$R^4$ and $R^5$ are independently hydrogen, $C_{1-6}$alkyl, $C_{3-7}$cycloalkyl, heterocyclylalkyl, or $R^4$ and $R^5$ together with the N to which they are attaches form a heterocyclyl;

$R^6$ is $C_{1-6}$alkyl or $C_{3-7}$cycloalkyl; and $R^7$ and $R^8$ are independently hydrogen or $C_{1-6}$alkyl;

or pharmaceutically acceptable salts thereof.

In one embodiment, heterocyclyl, alone or as used in the terms heterocyclyl-$C_{1-6}$alkyl and —CONH—$C_{1-6}$alkl-heterocyclyl, is: piperidinyl, piperazinyl, homopiperazinyl, azepinyl, dioxolanyl, pyrrolidinyl, pyrazolidinyl, imidazolidinyl, imidazolinyl, pyridinyl, pyridazinyl, pyrimidinyl, oxazolidinyl, isoxazolyl, morpholinyl, thiazolidinyl, isothiazolyl, quinuclidinyl, thiadiazolyl, dihydrofuryl, tetrahydrofuranyl, dihydropyranyl, tetrahydropyranyl, thiomorpholinyl, thiomorpholinylsulfoxide, or thiomorpholinylsulfone.

In another embodiment, $R^1$ and $R^2$ are F.

In another embodiment, one of X and $X^1$ is F while the other is hydrogen.

In another embodiment, A is N.

In another embodiment, G is CH.

In another embodiment, $R^3$ is $C_{1-6}$alkyl.

In another embodiment, $R^3$ is methyl.

In another embodiment, Ar is aryl or heteroaryl, optionally substituted with 1-3 substituents independent selected from: $C_{1-6}$alky, $C_{3-7}$cycloalkyl, halogen, cyano, —$CONR^4R^5$, —$NHCOR^6$, —$SO_2NR^7R^8$, $C_{1-6}$alkoxyl-$C_{1-6}$alkyl-, heterocyclyl, and heterocyclyl-$C_{1-6}$alkyl-.

In another embodiment, Ar is phenyl optionally substituted with 1-3 substituents independently selected from: $C_{1-6}$alky, $C_{3-7}$cycloalkyl, halogen, cyano, —$CONR^4R^5$, —$NHCOR^6$, —$SO_2NR^7R^8$, $C_{1-6}$alkoxyl-$C_{1-6}$alkyl-, heterocyclyl, and heterocyclyl-$C_{1-6}$alkyl-.

In another embodiment, phenyl is disubstituted with F and —$CONR^4R^5$.

In another embodiment, F is meta to the point of attachment and —$CONR^4R^5$ is para to the point of attachment.

In another embodiment, $R^4$ and $R^5$ are independently hydrogen, $C_{1-6}$alky, or $C_{3-7}$cycloalkyl.

In another embodiment, $R^4$ and $R^5$ together with the N to which they are attached form a heterocyclyl.

In another embodiment, the heterocyclyl is pyrrolidinyl, morpholinyl or methylpiperazinyl.

In another embodiment, Ar is heteroaryl selected from furyl, pyridyl, pyridazinyl, pyrimidinyl, pyrazinyl, thiazolyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, isoindolyl, thiazolyl, benzothiazolyl, isothiazolyl, benzoxazolyl, benzisoxazolyloxazolyl, and quinolyl, optionally substituted with 1-3 substituents independent selected from: $C_{1-6}$alkyl, $C_{3-7}$cycloalkyl, halogen, cyano, —$CONR^4R^5$, —$NHCOR^6$, —$SO_2NR^7R^8$, $C_{1-6}$ alkoxyl-$C_{1-6}$alkyl-, heterocyclyl, and heterocyclyl-$C_{1-6}$alkyl-.

In another embodiment, heteroaryl is pyridyl, optionally substituted with 1-3 substituents independent selected from: $C_{1-6}$alkyl, $C_{3-7}$cycloalky, halogen, cyano, —$CONR^4R^5$, —$NHCOR^6$, —$SO_2NR^7R^8$, $C_{1-6}$ alkoxyl-$C_{1-6}$alkyl-, heterocyclyl, and heterocyclyl-$C_{1-6}$alkyl-.

In another embodiment, pyridyl is monosubstituted with $C_{1-6}$alkyl, halogen, cyano, or —$CONR^4R^5$.

In another embodiment, $R^4$ and $R^5$ are independently hydrogen, $C_{1-6}$alky, or $C_{3-7}$cycloalkyl.

In another embodiment, pyridyl is monosubstituted with $C_{1-6}$alkyl, halogen, or cyano.

In another embodiment, the pyridyl ring N is meta to the point of attachment.

In another embodiment, heteroaryl is pyrazolyl, optionally substituted with 1-3 substituents independent selected from: $C_{1-6}$alkyl, $C_{3-7}$cycloalkyl, halogen, cyano, —$CONR^4R^5$, —$NHCOR^6$, —$SO_2NR^7R^8$, $C_{1-6}$alkoxy-$C_{1-6}$alkyl-, heterocyclyl, and heterocyclyl-$C_{1-6}$alkyl-.

In another embodiment, pyrazolyl is monosubstituted with $C_{1-6}$alkyl, $C_{3-7}$cycloalky, $C_{1-6}$alkoxy-$C_{1-6}$alkyl-, heterocyclyl, or heterocyclyl-$C_{1-6}$alkyl-.

In another embodiment, pyrazolyl is monosubstituted with $C_{1-6}$alkyl, $C_{3-7}$cycloalky, or $C_{1-6}$alkoxy-$C_{1-6}$alkyl-.

In another embodiment, pyrazolyl is monosubstituted with $C_{3-7}$cycloalky.

In another embodiment, pyrazolyl is monosubstituted with cyclopropyl.

In another embodiment, pyrazolyl is attached at the 4-position and substituted at the 1-position.

In another embodiment, J is CH.

In another embodiment, M is N.

In another embodiment, J is CH and M is N.

In another embodiment, J is CH, M is N and $R^3$ is $CH_3$.

The preferred compounds of this invention are Examples 1-52 as described herein.

It is understood that all chemically allowable combinations of the above embodiments are also contemplated as further embodiments of the present invention.

In a second aspect, the present invention provides methods for preparing compounds of Formula I, as demonstrated in the Examples. For example compounds of formula I can be prepared by the following synthesis routes:

1) Reaction of a Compound of Formula B with a Compound of Formula C:

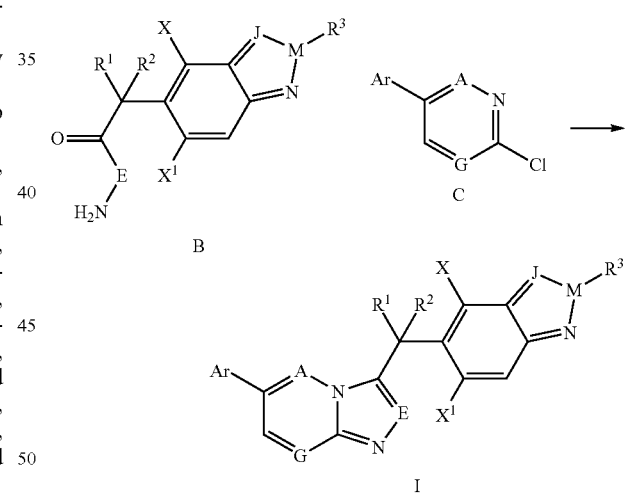

Wherein, A, Ar, E, G, J, M, $R^1$, $R^2$, $R^3$, X and $X^1$ are as defined herein.

2) Reaction of a Compound of Formula D with a Compound of Formula E:

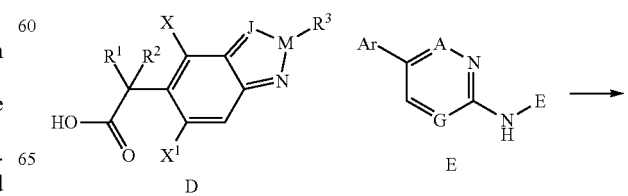

-continued

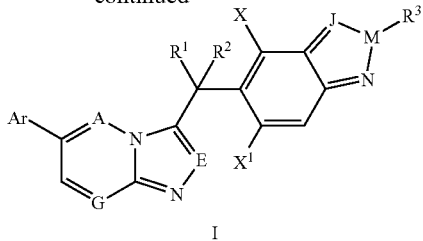

Wherein, A, Ar, E, G, J, M, R¹, R², R³, X and X¹ are as defined herein.

3) Reaction of a Compound of Formula F with a Compound of Formula G:

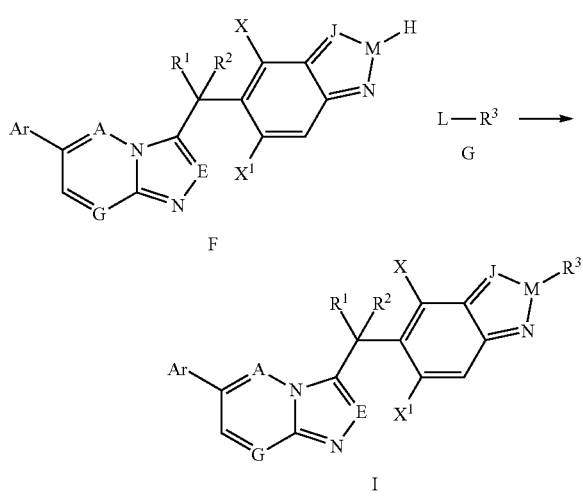

Wherein, A, Ar, E, G, J, M, R¹, R², R³, X and X¹ are as defined herein. L is a leaving group (such as, Cl, Br, phenoxide, 4-nitrophenoxide, 2,3-dichlorophenoxide etc.).

4) Reaction of a compound of formula H with a compound of formula J:

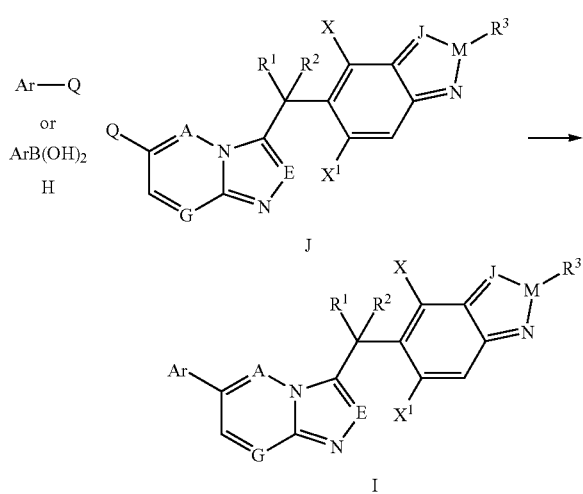

Wherein, A, Ar, E, G, J, M, R¹, R², R³, X and X¹ are as defined herein. Q is Cl, Br, or I.

5) Reaction of a Compound of Formula K with a Compound of Formula L:

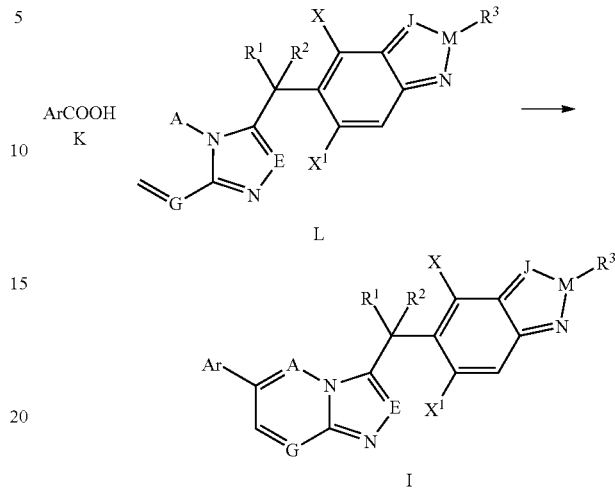

Wherein, A, Ar, E, G, J, M, R¹, R², R³, X and X¹ are as defined herein.

In a third aspect, the present invention provides pharmaceutical compositions comprising a compound of formula I, or a pharmaceutically acceptable salt thereof, together with a pharmaceutically acceptable carrier or excipient.

In a fourth aspect, the present invention provides a compound of formula I, or a pharmaceutically acceptable salt thereof, for use as a medicament.

In a fifth aspect, the present invention provides a compound of formula I, or a pharmaceutically acceptable salt thereof, for in the treatment of cancer.

In a sixth aspect, the present invention provides a method of treating cancer comprising administering to a mammal in need of such treatment a therapeutically effective amount of a compound of formula I, or a pharmaceutically acceptable salt thereof.

DETAILED DESCRIPTION

Unless otherwise noted, the following definitions of example illustrate and define the meaning and scope of various terms used in the present invention:

The terms "halogen" and "halo" refers to fluorine, chlorine, bromine and iodine; preferably fluorine, chlorine and bromine; and more preferably fluorine.

The term "$C_{1-6}$alkyl", alone or in combination with other groups, means a branched or straight chain monovalent alkyl containing 1-6 carbon atoms. Examples include methyl, ethyl, n-propyl, isopropyl, n-butyl, sec-butyl, and tert-butyl. $C_{1-4}$ alkyl is preferred.

"Halo$C_{1-6}$alkyl" refers to a $C_{1-6}$alkyl group as defined herein, wherein one or more hydrogens have been the independently replaced with a halogen. Examples include —$CH_2Cl$, —$CH_2CF_3$, —$CH_2CCl_3$, and perfluoroalkyl (e.g., —$CF_3$).

The term "$C_{3-7}$cycloalkyl", alone or in combination with other groups, refers to a saturated monovalent cyclic hydrocarbon group with 3-7 ring carbons, such as cyclopropyl, cyclobutyl, cyclopentyl, and cyclohexyl.

The term "$C_{1-6}$alkoxy", alone or in combination with other groups, refers to R'—O—, wherein R' is $C_{1-6}$alkyl.

The term "aryl", alone or in combination with other groups, means phenyl or naphthyl, preferably phenyl.

The term "heteocyclyl" alone or in combination with other groups, refers to 4-6 ring atoms of a non-aromatic monocyclic group, wherein one or two ring atoms are selected from N, O, or $S(O)_n$ (where n is an integer from 0 to 2) and the remaining ring atoms are C. Examples include: piperidinyl, piperazinyl, homopiperazinyl, azepinyl, dioxolanyl, pyrrolidinyl, pyrazolidinyl, imidazolidinyl, imidazolinyl, pyridinyl, pyridazinyl, pyrimidinyl, oxazolidinyl, isoxazolyl, morpholinyl, thiazolidinyl, isothiazolyl, quinuclidinyl, thiadiazolyl, dihydrofuryl, tetrahydrofuranyl, dihydropyranyl, tetrahydropyranyl, thiomorpholinyl, thiomorpholinylsulfoxide, and thiomorpholinylsulfone. Preferred groups are pyrrolidinyl, morpholinyl, piperazinyl, tetrahydrofuranyl, and dioxolanyl.

The term "heteroaryl" refers to an aromatic 5 to 6-membered monocyclic or 9 to 10-membered bicyclic, containing 1, 2 or 3 ring atoms independently selected from nitrogen, oxygen and sulfur. Examples include furyl, pyridyl, pyridazinyl, pyrimidinyl, pyrazinyl, thiazolyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, isoindolyl, thiazolyl, benzothiazolyl, isothiazolyl, benzoxazolyl, benzisoxazolyloxazolyl, and quinolyl. Preferred groups are pyrazolyl and pyridinyl.

It will be understood by the skilled artisan that the compounds of the present invention are capable of reaction with a number of inorganic and organic acids to form pharmaceutically acceptable acid addition salts. Such pharmaceutically acceptable acid addition salts and common methodology for preparing them are well known in the art. See, e.g., P. Stahl, et ah, HANDBOOK OF PHARMACEUTICAL SALTS: PROPERTIES, SELECTION AND USE, (VCHA/Wiley-VCH, 2002); and S. M. Berge, et ah, "Pharmaceutical Salts," Journal of Pharmaceutical Sciences, Vol. 66, No. 1, January 1977.

"Pharmaceutically acceptable salt" refers to conventional acid or base addition salts, which are formed by a suitable non-toxic organic or inorganic acid or an organic or inorganic base. Examples of inorganic acids include hydrochloric acid, hydrobromic acid, hydroiodic acid, sulfuric acid, sulfamic acid, phosphoric acid and nitric acid. Examples of organic acids include toluenesulfonic acid, salicylic acid, methanesulfonic acid, oxalic acid, succinic acid, citric acid, maleic acid, lactic acid, and fumaric acid. Examples of the alkali addition salts include salts derived from ammonium, potassium, sodium and quaternary ammonium hydroxides, such as tetramethylammonium hydroxide.

"Pharmaceutically acceptable" such as pharmaceutically acceptable carrier, excipient, etc., means for the subject of administration of the particular compound is a pharmaceutically acceptable and substantially non-toxic.

The compounds of the present invention have inhibitory activity on the c-Met kinase. These compounds may be used in the treatment of hyperproliferative diseases such as cancer and in particular colorectal, breast, lung, prostate cancer, pancreatic cancer, stomach cancer, bladder cancer, ovarian cancer, melanoma, neuroblastoma, cervical kidney cancer or kidney cancer, leukemia or lymphoma. Treatment includes acute—myeloid leukemia (AML, acute lymphocytic leukemia (ALL) and gastrointestinal stromal tumors (GIST).

In an alternative embodiment, the present invention includes a pharmaceutical composition, said pharmaceutical composition contains at least one compound of formula I or a pharmaceutically acceptable salt thereof, together with a pharmaceutically acceptable excipient and/or carrier.

The compounds of the present invention are preferably formulated as pharmaceutical compositions administered by a variety of routes. Such pharmaceutical compositions and processes for preparing them are well known in the art. See, e.g., REMINGTON: THE SCIENCE AND PRACTICE OF PHARMACY (A. Gennaro, et al., eds, $19^{th}$ ed. Mack Publishing Co., 1995)

These pharmaceutical compositions may be administered orally, e.g. in the form of tablets, coated tablets, dragees, hard or soft capsules, solutions, emulsions or suspensions. They can also be administered rectally, e.g. in the form of suppositories, or parent rally, for example, as injections form.

Prepared of the present invention is a pharmaceutical composition containing the compounds of formula I and/or a salt or ester thereof may be known to those skilled in the art, for example using conventional mixing, sealed capsules, dissolving, granulating, emulsifying, encapsulating system dragees or freeze-drying method; these pharmaceutical preparations and therapy of inert, inorganic or organic carrier formulation. Lactose, corn starch or derivatives thereof talc, stearic acid or its salts can be used for tablets, coated tablets, dragees and hard gelatine capsules the carrier. Suitable carriers for the preparation of soft capsules include vegetable oils, waxes, and the fat; Depending on the nature of the active ingredient, usually in the case of soft capsules, no carrier. Suitable carriers for preparing a solution or syrup, water, polyols, sucrose, invert sugar and glucose. Suitable carriers for injection of water, alcohols, polyols, glycerol, vegetable oils, phosphoric acid and the surface active agent. For suppositories suitable carrier is a natural oil, or hardened oil, wax, fat, and semi-solid polyol.

The pharmaceutical preparations may also contain preservatives, solubilizers, stabilizers, wetting agents, emulsifiers, sweeteners, coloring agents, flavoring agents, for changing a salt of the osmotic pressure, buffers, coating agents or antioxidants. They may also contain other therapeutically valuable substances, including additional active ingredients of the compounds of formula I with different biological active compounds.

As described herein, the compounds of the present invention, including the compounds of formula I can be used for the treatment or control of cell proliferative disorders. These compounds and formulations containing the compounds are particularly useful in the treatment or control of solid tumors, for example, breast, colon, lung and prostate tumors.

The "therapeutically effective amount" of a compound of this invention means an amount of the compound that effectively prevents or delays the progression of the disease, or attenuates, ameliorates some of the symptoms of the disease or extends the life of patients. Determination of therapeutically effective amount depends on a variety of factors well known in medical arts.

The effective amount or dose may be changed within wide limits, and may be known in the art to determine in accordance with the treatment of the compounds of the present invention. The dose in each particular case can be adjusted according to the individual need and the particular circumstances, including the specific compound administered, the route of administration, the case being treated and the patients being treated. Typically, to about 70 Kg adult oral or parenteral administrations, from about 10 mg to about 10,000 mg, preferably from about 100 mg to about 1,000 mg daily dose should be appropriate, although there are indications that can be exceeded the upper limit. The daily dose can be a single dose or separate doses, or for parenteral administration, can be given in the form of a continuous infusion.

EDCI means 1-Ethyl-3-(3-dimethylaminopropyl)carbodiimid;

DMF means dimethylformamide; HOBt means hydroxybenzotriazole;

THF means tetrahydrofuran;

DIPEA means N,N-diisopropylethylamine;

HATU means O-(7-azabenzotriazol-1-yl)-N,N,N',N'-tetramethyluronium hexafluorophosphate;

Pd$_2$(dba)$_3$ means tris(dibenzylideneacetone)dipalladium (0);

PCy$_3$ means tricyclohexylphosphine;

Pd(dppf)Cl$_2$ means [1,1'-Bis(diphenylphosphino)ferrocene]dichloropalladium(II);

18-crown-6 means 1,4,7,10,13,16-hexaoxacyclooctadecane;

DMSO means dimethyl sulfoxide;

and MS means ESI-MS (i.e., electrospray ionization mass spectrometry).

Preparation of Intermediates

Intermediates A

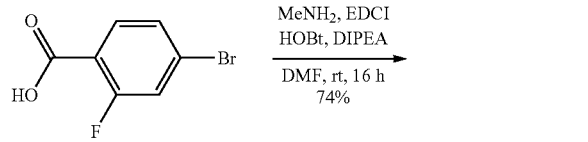

Step 1: 4-Bromo-2-fluoro-N-methylbenzamide

To a 100 mL flask is added 4-bromo-2-fluorobenzoic acid (3.0 g, 13.7 mmol), 2 M methylamine (34.3 mL, 68.5 mmol), EDCI (6.6 g, 34.25 mmol), HOBt (2.8 g, 20.6 mmol), N,N-diisopropylethylamine, and DMF (50 mL). The reaction mixture is stirred at room temperature for 16 hrs. Then water (50 mL) is added. The aqueous phase is isolated and extracted with ethyl acetate (3×50 mL). The combined organic phases are dried over anhydrous sodium sulfate, filtered, and concentrated. The residue is purified on a silica gel flash chromatography with ethyl acetate/petroleum ether (1:3) to yield the titled compound as a white solid (2.34 g, 74% yield). (MS: [M+1] 232)

Step 1: 4-Bromo-2-fluoro-benzoyl chloride

To a 100 mL flask is added 4-bromo-2-fluorobenzoic acid (5.0 g, 22.8 mmol) and sulfurous dichloride (50 mL). The reaction mixture is stirred at room temperature for 2 hrs. After removal of extra sulfurous dichloride, the residue (4.0 g, 74%) is used in the next step without further purification. (MS: [M+1] 239)

Step 2: 4-Bromo-2-fluoro-N,N-dimethylbenzamlde

To a 50 mL flask is added 4-bromo-2-fluorobenzoic chloride (4.0 g, 16.9 mmol), dimethyl amine (2 M, 13 mL, 10.8 mmol), cesium carbonate (11 g, 33.8 mmol), and THF (50 mL). The reaction mixture is stirred overnight; then brine (30 mL) is added. Aqueous phase is separated and extracted with ethyl acetate (3×50 mL). The combined organic phases are dried over anhydrous sodium sulfate, filtered, and concentrated. The residue is purified on a silica gel flash chromatography with ethyl acetate/petroleum ether (1:3) to give the product as a white solid (3.6 g, 88%). (MS: [M+1] 246)

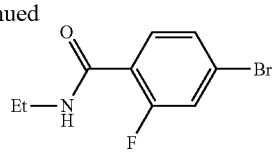

Step 1: 4-Bromo-2-fluoro-N-ethylbenzamide

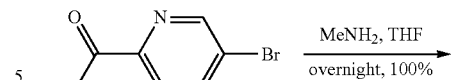

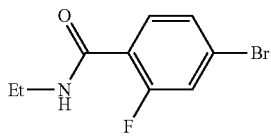

To a 100 mL flask is added 4-bromo-2-fluorobenzoic acid (0.767 g, 3.5 mmol), ethylamine (2 M, 3.5 mL, 7.0 mmol), HATU (1.65 g, 7.0 mmol), N,N-diisopropylethylamine (0.925 g, 7.0 mmol), and DMF (50 mL). The reaction mixture is stirred at room temperature for 2 hrs and followed by adding water (10 mL). The aqueous phase is isolated and extracted with ethyl acetate (3×10 mL). The combined organic phases are dried over anhydrous sodium sulfate, filtered, and concentrated. The residue is purified on a silica gel flash chromatography with ethyl acetate/petroleum ether (1:3) to obtain the desired compound as a white solid (0.80 g, 95% yield). (MS: [M+1] 246)

Step 1: 5-Bromo-N-methylpicolinamide

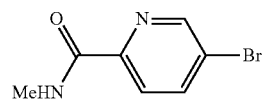

To a 50 mL flask is added methyl 5-bromopicolinate (2.0 g, 9.3 mmol) and methylamine (2 M, 18.5 mL, 37.0 mmol). The reaction mixture is stirred at room temperature overnight. After concentration, a white solid is obtained, which is used in next step without further purification (2.0 g, 100%). (MS: [M+1] 216)

The above methods are used to prepare the following intermediates A1-A14 (Table A1).

TABLE A1

Intermediates A1-A14

| Intermediate | Starting Material | Structure | Molecular Ion [M + 1]⁺ |
|---|---|---|---|
| A1 | Me—NH₂  HO-C(O)-C₆H₃(F)-Br | F-C₆H₃(Br)-C(O)-NHMe | 232.1 |
| A2 | Me—NH₂  HO-C(O)-C₆H₃(F)-Br | C(O)-NHMe C₆H₃(F)(Br) | 232.1 |
| A3 | iPr-NH₂  HO-C(O)-C₆H₃(F)-Br | C(O)-NH-iPr C₆H₃(F)(Br) | 260.1 |
| A4 | Me₂NH  HO-C(O)-C₆H₃(F)-Br | C(O)-NMe₂ C₆H₃(F)(Br) | 246.1 |

TABLE A1-continued

Intermediates A1-A14

| Intermediate | Starting Material | Structure | Molecular Ion [M + 1]+ |
|---|---|---|---|
| A5 | Et—NH₂ + 4-bromo-2-fluorobenzoic acid | N-ethyl-4-bromo-2-fluorobenzamide | 246.1 |
| A6 | isopropylamine + 4-bromo-2-fluorobenzoic acid | N-isopropyl-4-bromo-2-fluorobenzamide | 260.1 |
| A7 | cyclopropylamine + 4-bromo-2-fluorobenzoic acid | N-cyclopropyl-4-bromo-2-fluorobenzamide | 258.1 |
| A8 | pyrrolidine + 4-bromo-2-fluorobenzoic acid | (4-bromo-2-fluorophenyl)(pyrrolidin-1-yl)methanone | 273.1 |
| A9 | morpholine + 4-bromo-2-fluorobenzoic acid | (4-bromo-2-fluorophenyl)(morpholino)methanone | 288.1 |
| A10 | 1-methylpiperazine + 4-bromo-2-fluorobenzoic acid | (4-bromo-2-fluorophenyl)(4-methylpiperazin-1-yl)methanone | 301.1 |
| A11 | Me—NH₂ + 4-bromo-2,6-difluorobenzoic acid | N-methyl-4-bromo-2,6-difluorobenzamide | 250.1 |
| A12 | cyclopropanecarboxylic acid + 4-bromo-2-fluoroaniline | N-(4-bromo-2-fluorophenyl)cyclopropanecarboxamide | 258.1 |

TABLE A1-continued

Intermediates A1-A14

| Intermediate | Starting Material | Structure | Molecular Ion [M + 1]+ |
|---|---|---|---|
| A13 | Me—NH$_2$, 4-bromopyridine-2-carboxylic acid | N-methyl 4-bromopyridine-2-carboxamide | 215.1 |
| A14 | Me—NH$_2$, 5-bromopyridine-2-carboxylic acid | N-methyl 5-bromopyridine-2-carboxamide | 215.1 |

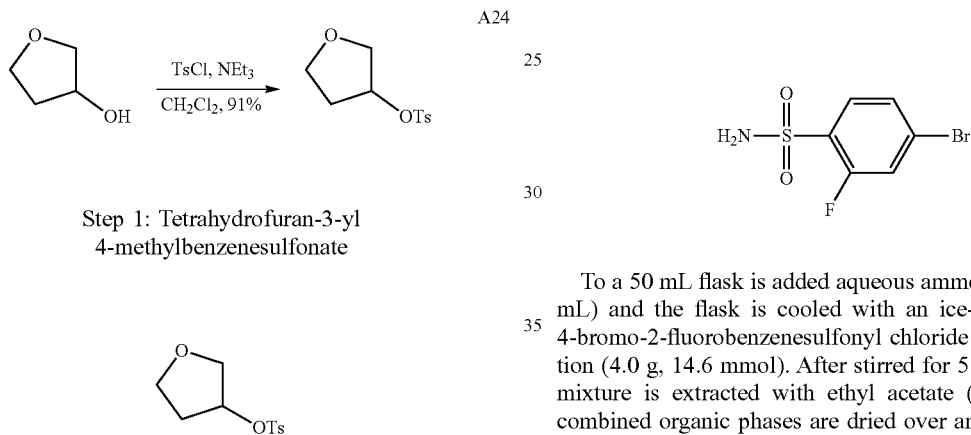

Step 1: Tetrahydrofuran-3-yl 4-methylbenzenesulfonate

To a 50 mL flask is added tetrahydrofuran-3-ol (1.0 g, 11.4 mmol), 4-methylbenzene-1-sulfonyl chloride (2.42 g, 13.7 mmol), triethylamine (4.6 g, 45.4 mmol), and dichloromethane (10 mL). The reaction mixture is stirred at room temperature overnight, diluted with dichloromethane (50 mL), and washed with water (2×10 mL). The organic phase is isolated, dried over anhydrous sodium sulfate, filtered, and concentrated. The residue is purified on a silica gel flash chromatography with ethyl acetate/petroleum ether (1:5) to give the titled compound (2.3 g, 91% yield). (MS: [M+1] 243)

Step 1: 4-Bromo-2-fluorobenzamide

To a 50 mL flask is added aqueous ammonia solution (60 mL) and the flask is cooled with an ice-salt bath. Then, 4-bromo-2-fluorobenzenesulfonyl chloride is added in portion (4.0 g, 14.6 mmol). After stirred for 5 hrs, the reaction mixture is extracted with ethyl acetate (4×50 mL). The combined organic phases are dried over anhydrous sodium sulfate, filtered, and concentrated to give a white solid (3.7 g, 100% yield). It is used in next step without further purification. (MS: [M+1] 254)

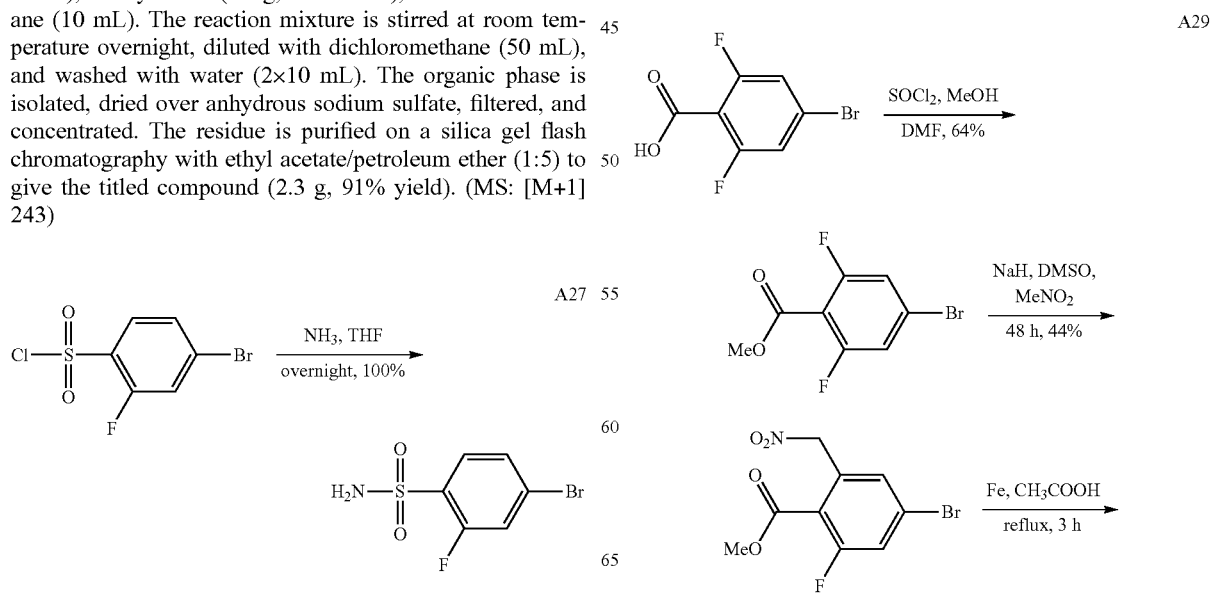

-continued

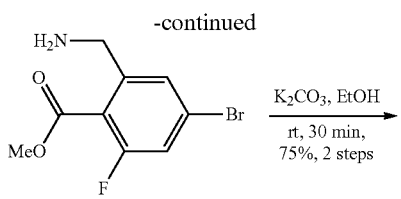

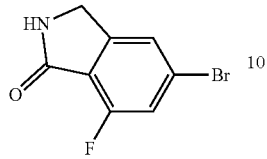

Step 1: Methyl 4-bromo-2,6-difluorobenzoate

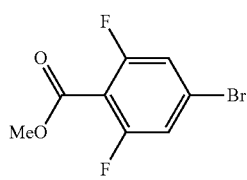

To a 100 mL flask is added 4-bromo-2,6-difluorobenzoic acid (5.0 g, 21.1 mmol), dichloromethane (20 mL), sulfurous dichloride (15 mL), and DMF (0.5 mL). The reaction mixture is stirred at room temperature for 2.5 hrs and then cooled to 0° C., followed by addition of methanol dropwise (20 mL). After 3 hrs, water (50 mL) and dichloromethane (50 mL) are added. The organic phase is isolated, washed with aqueous saturated sodium bicarbonate solution (50 mL) and brine (50 mL), dried over anhydrous sodium sulfate, filtered, and concentrated to yield a brown solid (3.39 g, 64% yield), which is used in next step without purification. (MS: [M+1] 251)

Step 2: Methyl 4-bromo-2-fluoro-6-nitromethylbenzoate

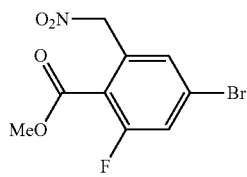

To a 50 mL flask is added nitromethane (1.0 mL, 16.9 mmol), anhydrous magnesium sulfate (4.0 g), DMSO (15 mL), and in portion sodium hydride (405 mg, 16.9 mmol). After 30 min, methyl 4-bromo-2,6-difluorobenzoate (530 mg, 2.1 mmol) is added. After stirring for 2 days, water (80 mL) and aqueous hydrochloric acid (6 M, 50 mL) are added, followed by dichloromethane (100 mL). The aqueous layer is separated and extracted with dichloromethane (2×50 mL). The combined organic phases are washed with brine (50 mL), dried over anhydrous sodium sulfate, filtered, and concentrated. The residue is purified on a silica gel flash chromatography with ethyl acetate/petroleum ether (1:30) to provide the titled compound as a light yellow solid (270 mg, 44% yield). (MS: [M+1] 292)

Steps 3 and 4: 5-Bromo-7-fluoroisoindolin-1-one

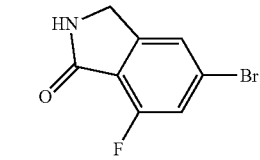 [SMILES: O=C1NCc2cc(Br)cc(F)c21]

To a 100 mL flask is added water (20 mL), ethanol (60 mL), methyl 4-bromo-2-fluoro-6-nitromethylbenzoate (500 mg, 1.71 mmol), and iron powder (959 mg, 17.1 mmol). The reaction mixture is stirred at reflux for 3 hrs, cooled to room temperature, filtrated, and concentrated. The residue is dissolved in ethanol (50 mL), followed by addition of potassium carbonate (1.0 g, 7.2 mmol). The reaction mixture is stirred at room temperature for 30 min, filtered, and concentrated to give a white solid (330 mg, 44% yield). It is used in next step without purification. (MS: [M+1] 230)

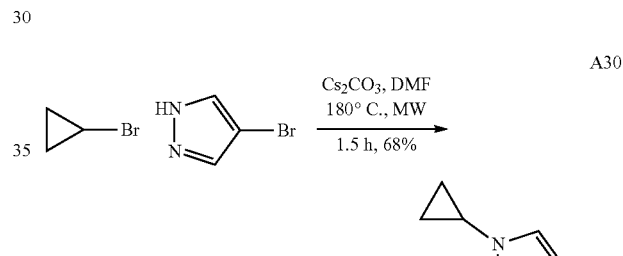

A30

Step 1: 4-Bromo-1-cyclopropyl-1-hydropyrrazole

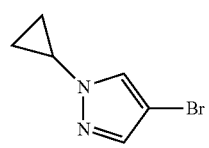

A mixture of 4-bromo-1H-pyrrazole (1.0 g, 6.8 mmol), bromocyclopropane (1.3 g, 10.7 mmol), cesium carbonate (3.5 g, 10.7 mmol), and DMF (6 mL) in a 30 mL microwave vial is heated to 180° C. under radiation for 1.5 hr. After cooled to room temperature, the reaction mixture is filtered. The filtrate is concentrated and the residue is purified on a silica gel flash chromatography with ethyl acetate/petroleum ether (1:5) to get a brown liquid (0.87 g, 68% yield). (MS: [M+1] 259)

The above methods are used to prepare intermediates A24, 26-A31 (Table A2).

TABLE A2

Intermediates A24, A26-A31

| Intermediate | Starting material | Structure | Molecular ion [M + 1]+ |
|---|---|---|---|
| A24 | tetrahydrofuran-3-ol | tetrahydrofuran-3-yl tosylate | 243.1 |
| A26 | (1,3-dioxolan-4-yl)methanol | (1,3-dioxolan-4-yl)methyl tosylate | 259.1 |
| A27 | NH₃, 4-bromo-2-fluorobenzenesulfonyl chloride | 4-bromo-2-fluorobenzenesulfonamide | 255.1 |
| A28 | MeNH₂, 4-bromo-2-fluorobenzenesulfonyl chloride | 4-bromo-2-fluoro-N-methylbenzenesulfonamide | 269.1 |
| A29 | 4-bromo-2,6-difluorobenzoic acid | 6-bromo-4-fluoroisoindolin-1-one | 230.1 |
| A30 | cyclopropyl bromide, 4-bromo-1H-pyrazole | 4-bromo-1-cyclopropyl-1H-pyrazole | 187.0 |
| A31 | cyclopropyl bromide, 1H-pyrazole-4-carboxylic acid | 1-cyclopropyl-1H-pyrazole-4-carboxylic acid | 153.1 |

Intermediates B

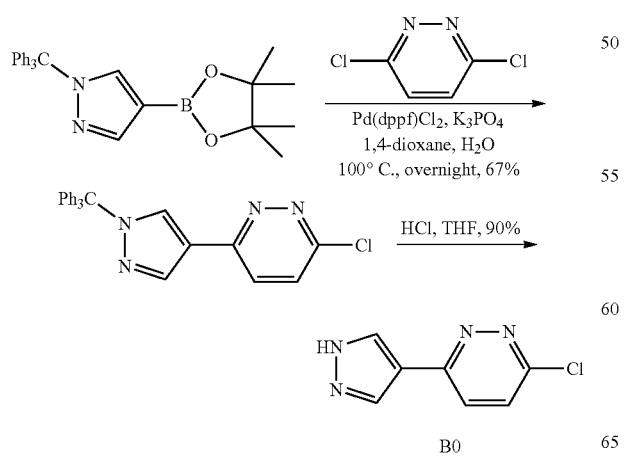

Step 1:
3-Chloro-6-(1-trityl-1H-pyrazol-4-yl)pyridazine

To a 100 mL flask is added 3-(4,4,5,5-tetramethyl-1,3,2-dioxaborolan-2-yl)-1-trityl-1H-pyrazole (20 g, 45.9 mmol), 3,6-dichloropyridazine (10.2 g, 68.5 mmol), Pd(dppf)Cl₂ (1.0 g, 1.4 mmol), potassium phosphate (26.4 g, 115 mmol), 1,4-dioxane (300 mL), and water (30 mL). The reaction mixture is stirred at 100° C. overnight under nitrogen, filtered, and concentrated. The residue is purified on a silica gel flash chromatography with ethyl acetate/petroleum ether (1:4) to give the title compound as a brown solid (13 g, 67% yield). (MS: [M+1] 423)

Step 2: 3-Chloro-6-(1H-pyrazol-4-yl)pyridazine

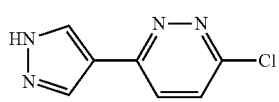 [SMILES: Clc1ccc(-c2cn[nH]c2)nn1]

To a 250 mL flask is added 3-chloro-6-(1-trityl-1H-pyrazol-4-yl) pyridazine (13 g, 30.8 mmol), THF (100 mL), and concentrated hydrochloric acid (50 mL). the reaction mixture is stirred at room temperature for 4 hrs and concentrated. The residue is treated with aqueous saturated sodium bicarbonate to pH 8-9, filtered, and concentrated to give a brown solid (5 g, 90%). (MS: [M+1] 181)

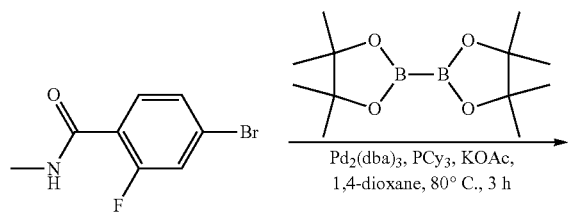

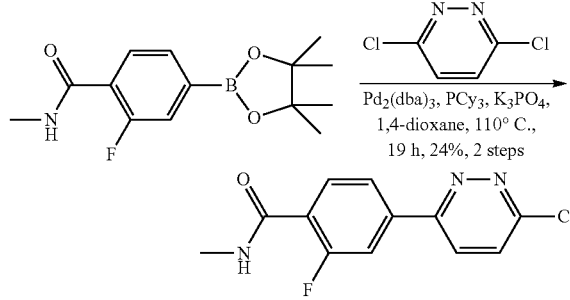

B1

Step 1: 2-Fluoro-N-methyl-4-(4,4,5,5-tetramethyl-1,3,2-dioxaborolan-2-yl)benzamide

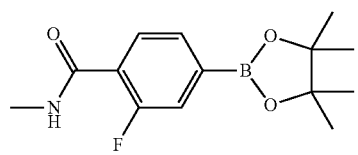

To a 100 mL flask is added 4-bromo-2-fluoro-N-methyl-benzamide (2.34 g, 10 mmol), 4,4,4',4',5,5,5',5'-octamethyl-2,2'-bis(1,3,2-dioxaborolane) (3.05 g, 12.0 mmol), $Pd_2$(dba)$_3$ (275 mg, 0.03 mmol), PCy$_3$ (168 mg, 0.06 mmol), potassium acetate (2.95 g, 30.0 mmol), and 1,4-dioxane (25 mL). The reaction mixture is stirred at 80° C. for 3 hrs under nitrogen and concentrated. The residue is treated with water (50 mL) and extracted with ethyl acetate (3×50 mL). The combined organic phases are washed with brine (50 mL), dried over anhydrous sodium sulfate, filtered, and concentrated. The crude product is used in next step without purification. (MS: [M+1] 280)

Step 2: 2-Chloro-6-(3-fluoro-N-methyl-4-benzamide)pyridazine

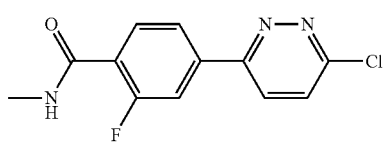 [SMILES: CNC(=O)c1ccc(-c2ccc(Cl)nn2)cc1F]

To a 100 mL flask is added 2-fluoro-N-methyl-4-(4,4,5,5-tetramethyl-1,3,2-dioxaborolan-2-yl)benzamide (10 mmol), 3,6-dichloropyridazine (2.23 g, 15.0 mmol), Pd$_2$(dba)$_3$ (275 mg, 0.03 mmol), PCy$_3$ (168 mg, 00.6 mmol), potassium phosphate (4.60 g, 20.0 mmol), 1,4-dioxane (20 mL), and water (5 mL). The reaction mixture is stirred at 110° C. under nitrogen overnight and concentrated. The residue is treated with water (50 mL) and extracted with ethyl acetate (3×50 mL). The combine organic layers are washed with brine (2×50 mL), dried over anhydrous sodium sulfate, filtered, and concentrated. The residue is purified on a silica gel flash chromatography with ethyl acetate/petroleum ether (1:2) to give the desired product as a brown solid (675 mg, 24% yield for 2 steps). (MS: [M+1] 266)

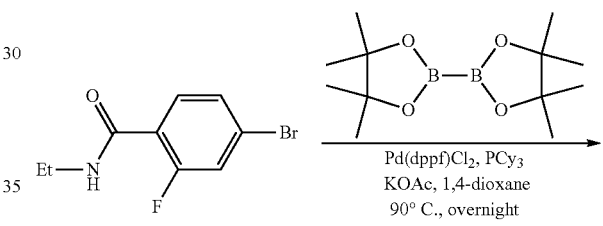

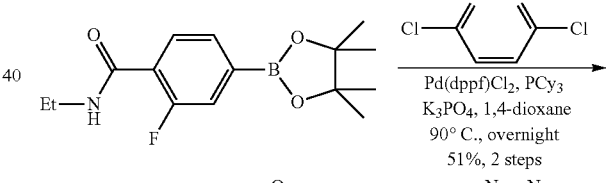

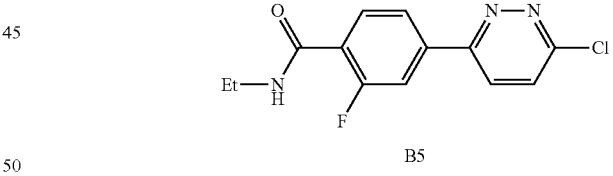

B5

Step 1: 2-Fluoro-N-ethyl-4-(4,4,5,5-tetramethyl-1,3-dioxaborolan-2-yl)benzamide

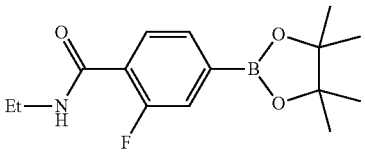 [SMILES: CCNC(=O)c1ccc(B2OC(C)(C)C(C)(C)O2)cc1F]

To a 50 mL flask is added 4-bromo-2-fluoro-N-ethylbenzamide (0.231 g, 0.94 mmol), 4,4,4',4',5,5,5',5'-octamethyl-2,2'-bis(1,3,2-dioxaborolane) (0.354 g, 1.41 mmol), Pd(dppf)Cl$_2$ (34 mg, 0.05 mmol), PCy$_3$ (36 mg, 0.09 mmol), potassium acetate (0.231 g, 2.35 mmol), and 1,4-dioxane (4 mL). The reaction mixture is stirred at 90° C. overnight, filtered, and concentrated. The crude product is used in next step without further purification. (MS: [M+1] 294)

Step 1:
2-Chloro-6-(3-fluoro-N-ethyl-4-benzamide)pridazine

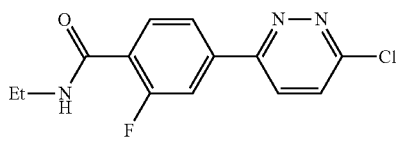 [SMILES: CCNC(=O)c1ccc(-c2ccc(Cl)nn2)cc1F]

To a 50 mL flask is added 2-fluoro-N-ethyl-4-(4,4,5,5-tetramethyl-1,3,2-dioxaborolan-2-yl)benzamide (0.94 mmol), 3,6-dichloropyridazine (0.282 g, 1.9 mmol), Pd(dppf)Cl$_2$ (34 mg, 0.05 mmol), PCy$_3$ (26 mg, 0.09 mmol), potassium phosphate (0.433 g, 1.9 mmol), 1,4-dioxane (5 mL), and water (0.5 mL). The reaction mixture is stirred at 90° C. overnight, filtered, and concentrated. The residue is purified on a silica gel flash chromatography with ethyl acetate/petroleum ether (1:1) to provide the titled compound as a brown solid (133 mg, 51% yield for 2 steps). (MS: [M+1] 280)

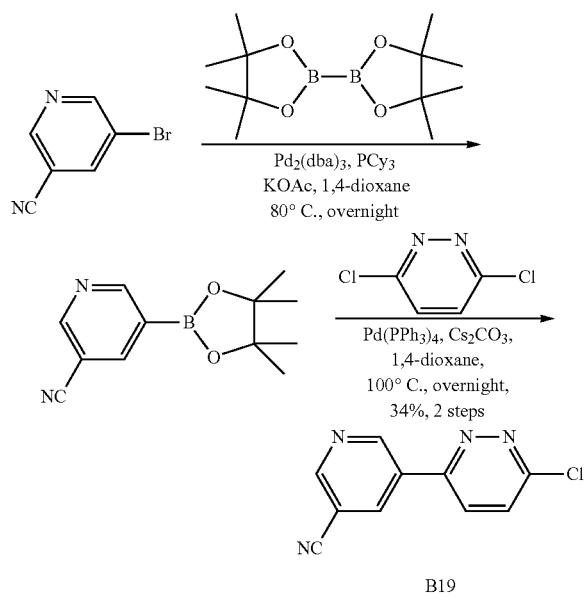

Step 1: 3-Cyano-5-(4,4,5,5-tetramethyl-1,3,2-dioxaborolan-2-yl)pyridine

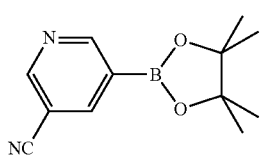 [SMILES: CC1(C)OB(c2cncc(C#N)c2)OC1(C)C]

To a 50 mL flask is added 5-bromo-3-cyanopyridine (0.50 g, 2.7 mmol), 4,4,4',4',5,5,5',5'-octamethyl-2,2'-bis(1,3,2-dioxaborolane) (0.832 g, 3.3 mmol), Pd$_2$(dba)$_3$ (75 mg, 0.08 mmol), PCy$_3$ (46 mg, 0.16 mmol), potassium acetate (0.803 g, 3.0 mmol), and 1,4-dioxane (10 mL). The reaction mixture is stirred at 80° C. overnight. Then, it is treated with water (40 mL), and extracted with ethyl acetate (3×30 mL). The organic layer is isolated, dried over anhydrous sodium sulfate, filtered, and concentrated. The residue is used in next reaction without further purification. (MS: [M+1] 231)

Step 2: 2-Chloro-6-(5-cyanopyridin-3-yl)pyridazine

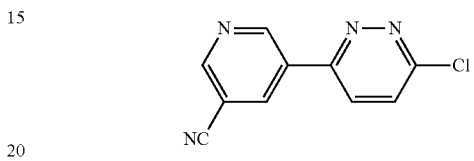

To a 50 mL flask is added 4-(4,4,5,5-tetramethyl-1,3,2-dioxaborolan-2-yl)-3-cyanopyridine (0.523 g, 2.7 mmol), 3,6-dichloropyridazine (0.611 g, 4.1 mmol), Pd(PPh$_3$)$_4$ (158 mg, 0.014 mmol), cesium carbonate (1.78 g, 5.5 mmol), and 1,4-dioxane (20 mL). The reaction mixture is stirred at 100° C. overnight, filtered, and concentrated. The residue is purified on a silica gel flash chromatography with ethyl acetate/petroleum ether (1:1) to obtain the desired product as a brown solid (200 mg, 34% combined yield). (MS: [M+1] 217)

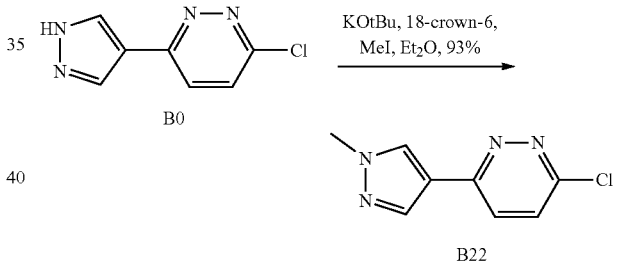

Step 1:
3-Chloro-6-(1-methyl-1H-pyrazol-4-yl)pyridazine

To a 100 mL flask is added 3-chloro-6-(1H-pyrazol-4-yl)pyridazine (1.7 g, 9.4 mmol), potassium tert-butoxide (1.23 g, 10.4 mmol), 18-crown-6 (250 mg, 0.94 mmol), and ether (40 mL). The reaction mixture is stirred at room temperature for 20 min and then cooled to 0° C., followed by addition of iodomethane dropwise (1.56 g, 10.9 mmol). The mixture is allowed to warm up to room temperature and stirred overnight. Then ice-water (30 mL) is added and the mixture is extracted with dichloromethane (3×50 mL). The combined organic phases are dried over anhydrous sodium sulfate, filtered, and concentrated to give the titled compound as a brown solid (1.7 g, 93% yield). (MS: [M+1] 195)

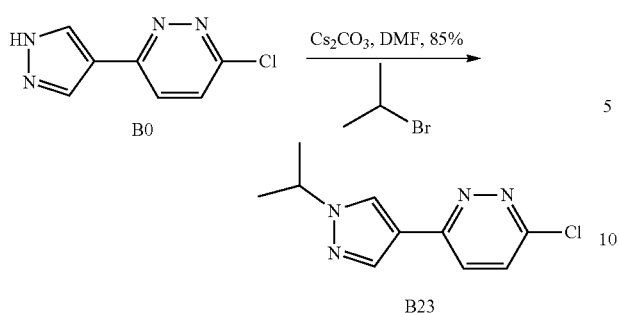

Step 1: 3-Chloro-6-(1-(tetrahydrofurane-3-yl)-1H-pyrazol-4-yl)pyridazine

To a 100 mL flask is added 3-chloro-6-(1H-pyrazol-4-yl)pyridazine (300 mg, 1.7 mmol), 2-bromopropane (820 mg, 6.7 mmol), cesium carbonate (2.77 g, 8.5 mmol), and DMF (50 mL). The reaction mixture is stirred at room temperature overnight, then treated with water (20 mL), and extracted with ethyl acetate (2×20 mL). The combined organic phases are dried over anhydrous sodium sulfate, filtered, and concentrated to yield the desired product (314 mg, 85% yield). (MS: [M+1] 223)

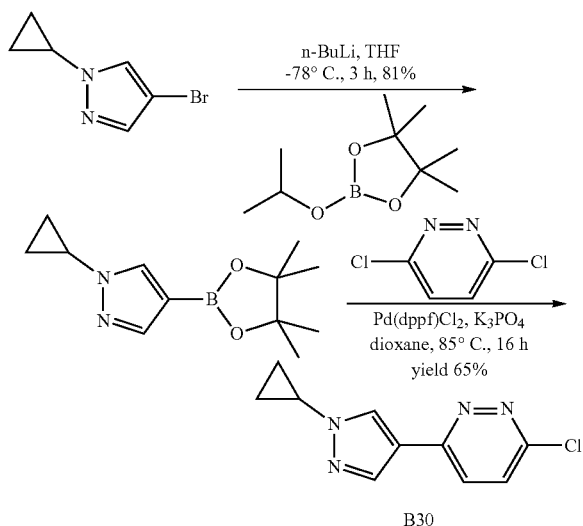

Step 1: 1-Cyclopropyl-4-(4,4,5,5-tetramethyl-1,3,2-dioxaborolan-2-yl)-1H-pyridazine

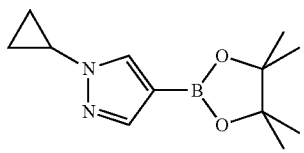 [SMILES: CC1(C)OB(c2cnn(C3CC3)c2)OC1(C)C]

To a 100 mL flask is added 4-bromo-1-cyclopropylpyrazol (6.57 g, 35.1 mmol) and anhydrous THF (30 mL). The solution is cooled to −78° C. under nitrogen; then n-butyl lithium (15.5 mL, 2.5 M in hexanes, 38.6 mmol) is added dropwise. The reaction mixture is stirred at the temperature for 1 hr, followed by addition of isopropyl boronate (9.17 g, 94.1 mmol) and stirred below −70° C. for 3 hours. The reaction is quenched with water (20 mL) and the resulted mixture is adjusted to pH 8-9 with aqueous hydrochloride solution (1 N). The combined organic phases are concentrated and used in next step without further purification (6.64 g, 81% yield). (MS: [M+1] 235)

Step 2: 3-Chloro-6-(1-cyclopropyl-1H-pyrazol-4-yl)pyridazine

To a 100 mL round bottom flask is added the above solid (6.64 g, 28.4 mol), 3,6-dichoropyridazine (8.46 g, 56.8 mmol), Pd(dppf)Cl$_2$ (1.04 g, 1.42 mol) potassium phosphate (18.1 g, 85.2 mmol), water (5 mL), and 1,4-dioxane (50 g) at room temperature under nitrogen. The reaction mixture is stirred at 90° C. overnight. After cooled to 30° C., water (20 mL) is added. The aqueous phase is isolated and extracted with ethyl acetate (3×30 mL). The combined organic phases are concentrated and the residue is purified on a silica gel flash chromatography to provide a yellow solid (4.07 g, 65% yield). (MS: [M+1] 222)

The above methods are used to prepare intermediates B0-B32 (Table B).

TABLE B

Intermediates B0 to B32

| Intermediate code | Starting Material structure | Structure | Molecular ion [M + 1]⁺ |
|---|---|---|---|
| B0 | Ph$_3$C-pyrazole-Bpin | HN-pyrazole-pyridazine-Cl | 181.1 |

TABLE B-continued

Intermediates B0 to B32

| Inter-mediate | Starting Material code | Starting Material structure | Structure | Molecular ion [M + 1]+ |
|---|---|---|---|---|
| B1 | A1 | 4-bromo-2-fluoro-N-methylbenzamide | 6-chloro-3-(3-fluoro-4-(methylcarbamoyl)phenyl)pyridazine | 266.1 |
| B2 | A2 | 4-bromo-3-fluoro-N-methylbenzamide | 6-chloro-3-(2-fluoro-4-(methylcarbamoyl)phenyl)pyridazine | 266.1 |
| B3 | A3 | 4-bromo-3-fluoro-N-isopropylbenzamide | 6-chloro-3-(2-fluoro-4-(isopropylcarbamoyl)phenyl)pyridazine | 294.1 |
| B4 | A4 | 4-bromo-2-fluoro-N,N-dimethylbenzamide | 6-chloro-3-(3-fluoro-4-(dimethylcarbamoyl)phenyl)pyridazine | 280.1 |
| B5 | A5 | 4-bromo-2-fluoro-N-ethylbenzamide | 6-chloro-3-(3-fluoro-4-(ethylcarbamoyl)phenyl)pyridazine | 280.1 |
| B6 | A6 | 4-bromo-2-fluoro-N-isopropylbenzamide | 6-chloro-3-(3-fluoro-4-(isopropylcarbamoyl)phenyl)pyridazine | 294.1 |
| B7 | A7 | 4-bromo-N-cyclopropyl-2-fluorobenzamide | 6-chloro-3-(4-(cyclopropylcarbamoyl)-3-fluorophenyl)pyridazine | 292.1 |
| B8 | A8 | (4-bromo-2-fluorophenyl)(pyrrolidin-1-yl)methanone | (4-(6-chloropyridazin-3-yl)-2-fluorophenyl)(pyrrolidin-1-yl)methanone | 306.1 |

TABLE B-continued

Intermediates B0 to B32

| Intermediate | Starting Material code | Starting Material structure | Structure | Molecular ion [M + 1]⁺ |
|---|---|---|---|---|
| B9 | A9 | | | 322.1 |
| B10 | A10 | | | 335.1 |
| B11 | A11 | | | 284.1 |
| B12 | A12 | | | 292.1 |
| B13 | A13 | | | 249.2 |
| B14 | A14 | | | 249.1 |
| B15 | | | | 192.1 |
| B16 | | | | 206.1 |
| B17 | | | | 210.1 |

TABLE B-continued

Intermediates B0 to B32

| Intermediate | Starting Material code | Starting Material structure | Structure | Molecular ion [M + 1]+ |
|---|---|---|---|---|
| B18 | | 3-bromo-5-chloropyridine | 3-(5-chloropyridin-3-yl)-6-chloropyridazine | 226.1 |
| B19 | | 5-bromo-nicotinonitrile | 5-(6-chloropyridazin-3-yl)nicotinonitrile | 217.1 |
| B20 | | 5-bromo-2-cyanopyridine | 5-(6-chloropyridazin-3-yl)picolinonitrile | 217.1 |
| B21 | | 4-bromo-2-methylpyridine | 4-(6-chloropyridazin-3-yl)-2-methylpyridine | 206.1 |
| B22 | B0 | 4-(6-chloropyridazin-3-yl)-1H-pyrazole + MeI | 3-chloro-6-(1-methyl-1H-pyrazol-4-yl)pyridazine | 195.2 |
| B23 | B0 | 4-(6-chloropyridazin-3-yl)-1H-pyrazole + 2-bromopropane | 3-chloro-6-(1-isopropyl-1H-pyrazol-4-yl)pyridazine | 223.1 |
| B24 | B0 | 4-(6-chloropyridazin-3-yl)-1H-pyrazole + bromocyclopentane | 3-chloro-6-(1-(tetrahydrofuran-3-yl)-1H-pyrazol-4-yl)pyridazine | 251.1 |
| B25 | B0 | 4-(6-chloropyridazin-3-yl)-1H-pyrazole + 1-bromo-2-methoxyethane | 3-chloro-6-(1-(2-methoxyethyl)-1H-pyrazol-4-yl)pyridazine | 239.1 |
| B26 | B0 | 4-(6-chloropyridazin-3-yl)-1H-pyrazole + 4-(bromomethyl)-1,3-dioxolane | 3-chloro-6-(1-((1,3-dioxolan-4-yl)methyl)-1H-pyrazol-4-yl)pyridazine | 267.1 |
| B27 | A27 | 4-bromo-2-fluorobenzenesulfonamide | 4-(6-chloropyridazin-3-yl)-2-fluorobenzenesulfonamide | 288.1 |

TABLE B-continued
Intermediates B0 to B32
| Intermediate | code | Starting Material structure | Structure | Molecular ion [M + 1]+ |
|---|---|---|---|---|
| B28 | A28 | | 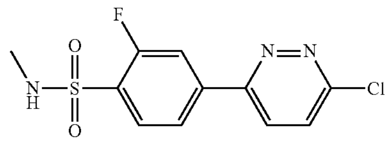 [SMILES: CNS(=O)(=O)c1ccc(-c2ccc(Cl)nn2)cc1F] | 302.1 |
| B29 | A29 | | 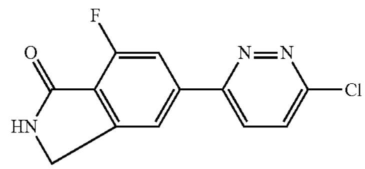 [SMILES: O=C1NCc2cc(-c3ccc(Cl)nn3)cc(F)c21] | 264.2 |
| B30 | A30 | | 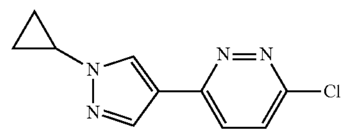 [SMILES: Clc1ccc(-c2cnn(C3CC3)c2)nn1] | 221.1 |
| B31 | | | 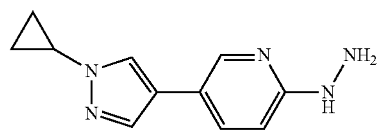 [SMILES: NNc1ccc(-c2cnn(C3CC3)c2)cn1] | 216.1 |
| B32 | | | 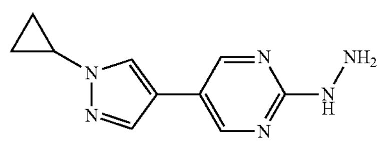 [SMILES: NNc1ncc(-c2cnn(C3CC3)c2)cn1] | 217.1 |
Intermediates C
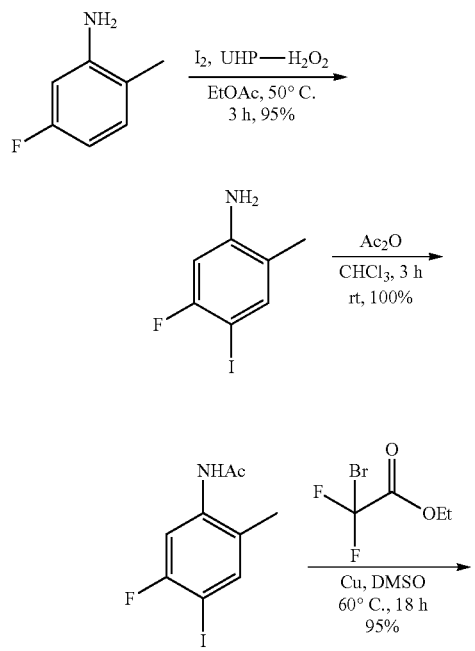
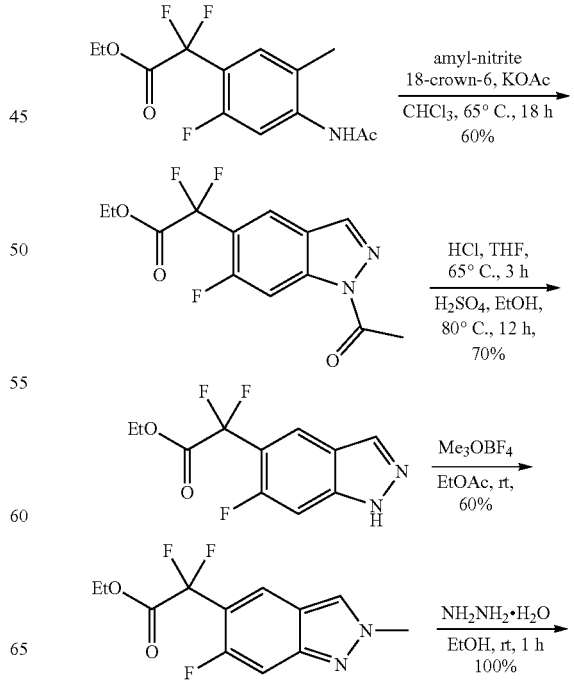

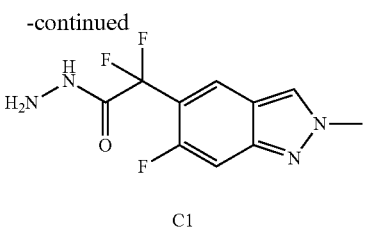

C1

Step 1: 5-Fluoro-4-iodo-2-methylaniline

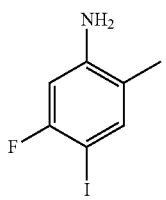

To a 1 L round bottom flask is added 5-fluoro-2-methylaniline (26.4 g, 211 mmol), ethyl acetate (500 mL), iodine (27.0 g, 106 mmol), and urea peroxide (14.8 g, 158 mmol). The reaction mixture is stirred at 50° C. for 3 hrs. After cooled to room temperature, it was added an aqueous saturated sodium hydrosulfite solution (300 mL). The organic phase is isolated and concentrated to provide a brown liquid (53.0 g, 100%). It is used in next step without further purification. (MS: [M+1] 252)

Step 2: N-(5-Fluoro-4-iodo-2-methylphenyl)acetamide

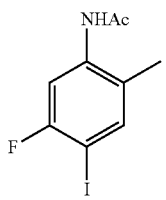

To a 1 L round bottom flask is added 5-fluoro-4-iodo-2-methylaniline (53.0 g, 211 mmol), acetic anhydride (23.7 g, 232 mmol), and chloroform (500 mL). The reaction mixture is stirred at room temperature for 3 hr. After removal of solvent a dark brown solid is obtained. It is used in next step without further purification (61.7 g, 100%). (MS: [M+1] 294)

Step 3: Ethyl 2-(4-acetamido-2-fluoro-5-methylphenyl)-2,2-difluoroacetate

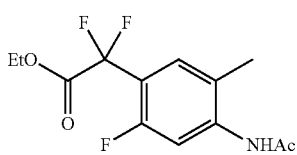 [SMILES: CCOC(=O)C(F)(F)c1cc(C)c(NC(C)=O)cc1F]

To a 1 L round bottom flask is added copper (powder, 54.0 g, 844 mmol), anhydrous dimethyl sulfoxide (500 mL), N-(5-fluoro-4-iodo-2-methylphenyl)acetamide (61.7 g, 211 mmol), and ethyl bromodifluoroacetate (64.3 g, 317 mmol) at room temperature under nitrogen. The reaction mixture is stirred at 60° C. for 18 hrs. After cooled to room temperature, it is added aqueous saturated solution of ammonium chloride (300 mL). The aqueous phase is isolated and extracted with ethyl acetate (3×300 mL). The combined organic phases are dried over anhydrous sodium sulfate. After removal of the solvent, the residue is purified on a silica gel flash chromatography with ethyl acetate/petroleum ether (1:2) to obtain a brown solid (60.9 g, 100% yield). (MS: [M+1] 290)

Step 4: Ethyl 2-(1-acetyl-6-fluoro-1H-indazol-5-yl)-2,2-difluoroacetate

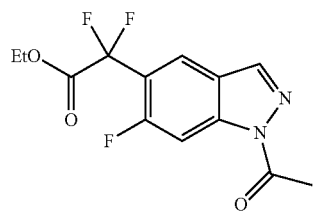 [SMILES: CCOC(=O)C(F)(F)c1cc2cnn(C(C)=O)c2cc1F]

To a 500 mL round bottom flask is added ethyl 2-(4-acetamido-2-fluoro-5-methylphenyl)-2,2-difluoroacetate (10.4 g, 35.8 mmol), chloroform (150 mL), isopentyl nitrite (9.23 g, 78.9 mmol), potassium acetate (7.02 g, 71.7 mmol), acetic anhydride (11.0 g, 108 mmol), and 18-crown-6 (1.83 g, 7.17 mmol) under nitrogen. The reaction mixture is stirred at 65° C. for 18 hrs. After cooled to room temperature, the solid is filtered off and the filtrate is concentrated. The residue is purified on a silica gel flash chromatography with ethyl acetate/petroleum ether (1:5) to give a light yellow solid (5.9 g, 55% yield). (MS: [M+1] 301)

Step 5: Ethyl 2-(6-fluoro-1H-indazol-5-yl)-2,2-difluoroacetate

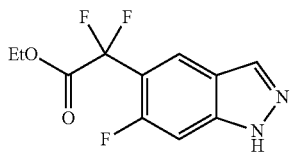 [SMILES: CCOC(=O)C(F)(F)c1cc2cn[nH]c2cc1F]

To a 1 L round bottom flask is added ethyl 2-(1-acetyl-6-fluoro-1H-indazol-5-yl)-2,2-difluoroacetate (67 g, 223 mmol) and THF (400 mL). Under well stirring, a concentrated aqueous hydrogen chloride acid solution (400 mL) is added dropwise. Then the reaction mixture is stirred at 65° C. for 3 hr. After removal of the solvent, absolute ethanol (800 mL) is added, followed by addition of concentrated sulfuric acid (40 mL) under well stirring. The resulting mixture is stirred at 80° C. for 12 h. After cooled to room temperature, aqueous saturated sodium bicarbonate solution (500 mL) is added. The aqueous phase is isolated and extracted with ethyl acetate (2×500 mL). The combined organic phases are dried over anhydrous sodium sulfate and concentrated. The residue is purified on a silica gel flash chromatography with ethyl acetate/petroleum ether (1:2) to yield a light yellow solid (40.3 g, 70%). (MS: [M+1] 259)

Step 6: Ethyl 2-(6-fluoro-2-methyl-1H-indazol-5-yl)-2,2-difluoroacetate

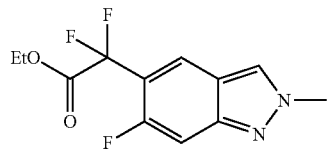 [SMILES: CCOC(=O)C(F)(F)c1cc2cn(C)nc2cc1F]

To a 100 mL round bottom flask is added ethyl 2-(1-acetyl-6-fluoro-1H-indazol-5-yl)-2,2-difluoroacetate (1.40 g, 5.4 mmol), ethyl acetate (40 mL), and trimethyloxonium tetrafluoroborate (1.2 g, 8.1 mmol). The reaction mixture is stirred at room temperature overnight. Then aqueous saturated sodium hydrosulfite solution (50 mL) is added. The aqueous phase is isolated and extracted with ethyl acetate (2×40 mL). The combined organic phases are washed with brine (50 mL), dried over anhydrous sodium sulfate, and concentrated. The residue is purified on a silica gel flash chromatography with ethyl acetate/petroleum ether (1:3) to get a yellow solid (1.3 g, 59% yield). (MS: [M+1] 273)

Step 7: 2,2-Difluoro-2-(6-fluoro-2-methyl-2H-indazol-5-yl)acetohydrazide

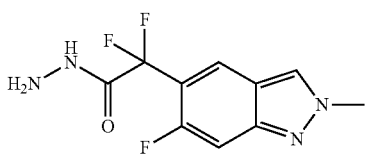 [SMILES: Cn1cc2cc(C(F)(F)C(=O)NN)c(F)cc2n1]

To a 100 mL flask is added ethyl 2-(6-fluoro-2-methyl-1H-indazol-5-yl)-2,2-difluoroacetate (2.13 g, 7.8 mmol), hydrazine (3.90 g, 78 mmol) and ethanol (20 mL). The reaction mixture is stirred at room temperature for 1 hr. After removal of solvents, a light yellow solid is obtained (2.01 g, 100% yield). It is used in next reaction without further purification. (MS: [M+1] 259)

The above methods are used to prepare intermediates C1-C5 (Table C).

TABLE C

Intermediates C1-C5

| Intermediates | Starting material | Structure | Molecular Ion [M + 1]+ |
|---|---|---|---|
| C1 | (4-fluoro-2-methylaniline) | (hydrazide indazole structure) | 259.1 |
| C2 | (3-fluoro-2-methylaniline) | (hydrazide indazole structure) | 259.1 |
| C3 | (3-fluoro-2-methylaniline) | (hydrazide indazole structure, NH) | 245.1 |
| C4 | (benzene-1,2-diamine) | (hydrazide benzimidazole structure, Ts) | 396.1 |
| C5 | (3,4-difluoronitrobenzene) | (hydrazide benzothiazole structure) | 241.1 |

EXAMPLES

Example 1

4-(3-(Difluoro(4-fluoro-2-methyl-2H-indazol-5-yl)methyl)-[1,2,4]triazolo[4,3-b]pyridazin-6-yl)-2-fluoro-N-methylbenzamide

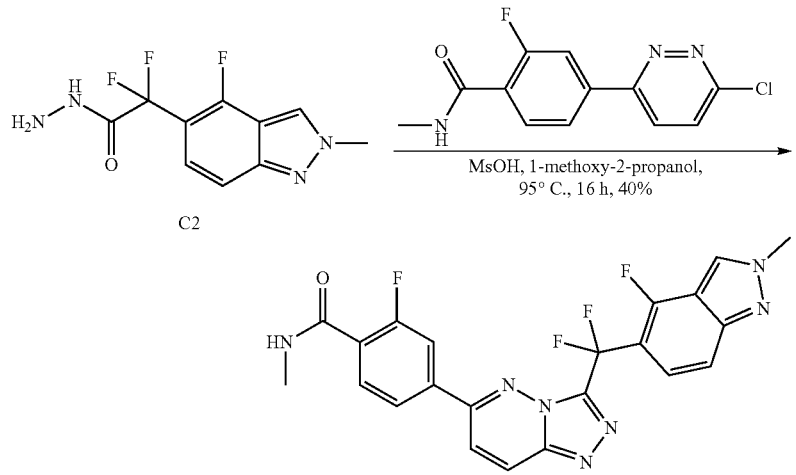

Example 1

To a 50 mL flask is added 2,2-difluoro-2-(4-fluoro-2-methyl-2H-indazol-5-yl)acetohydrazine (194 mg, 0.75 mmol), 4-(6-chloropyridazine-3-yl)-2-fluoro-N-methylbenzamide (199 mg, 0.75 mmol), methylsulfonic acid (0.06 mL, 0.9 mmol) and 1-methoxy-2-propanol (6 mL). The reaction mixture is stirred at 90° C. for 16 hrs and concentrated. The residue is purified on a silica gel flash chromatography with methanol/dichloromethane (1:20) to provide the desired compound as a light yellow solid (156 mg, 44% yield). (MS: [M+1] 470)

Examples 1-17 are prepared by using the above method from intermediate C2 (Table 1).

TABLE 1

Examples 1-17

| Example | Intermediate | Structure | Molecular Ion [M + 1]+ |
|---|---|---|---|
| 1 | B1 | 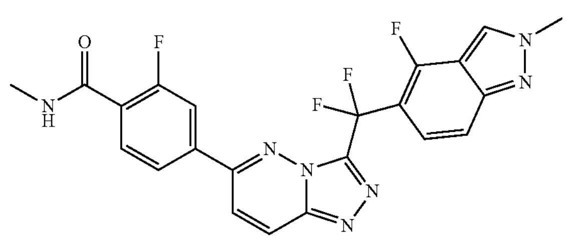 | 469.1 |
| 2 | B4 | 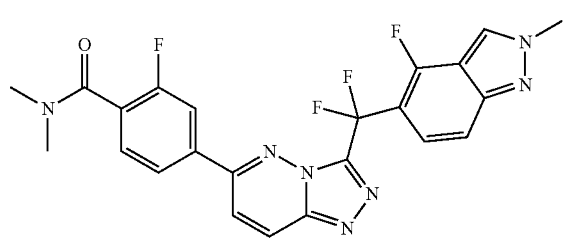 | 484.2 |

TABLE 1-continued

Examples 1-17

| Example | Intermediate | Structure | Molecular Ion [M + 1]+ |
|---|---|---|---|
| 3 | B5 | 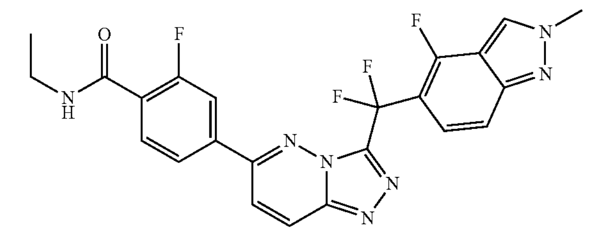 [SMILES: CCNC(=O)c1ccc(-c2ccc3nnc(C(F)(F)c4ccc5nn(C)cc5c4F)n3n2)cc1F] | 484.2 |
| 4 | B6 | 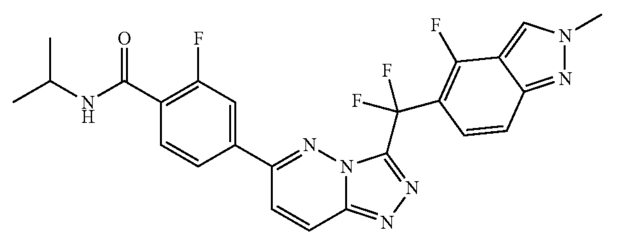 [SMILES: CC(C)NC(=O)c1ccc(-c2ccc3nnc(C(F)(F)c4ccc5nn(C)cc5c4F)n3n2)cc1F] | 498.2 |
| 5 | B7 | 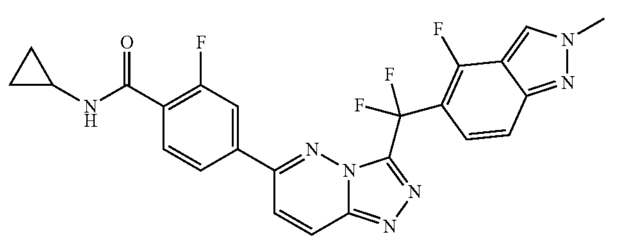 [SMILES: Cn1cc2c(F)c(C(F)(F)c3nnc4ccc(-c5ccc(C(=O)NC6CC6)c(F)c5)nn34)ccc2n1] | 496.2 |
| 6 | B11 | 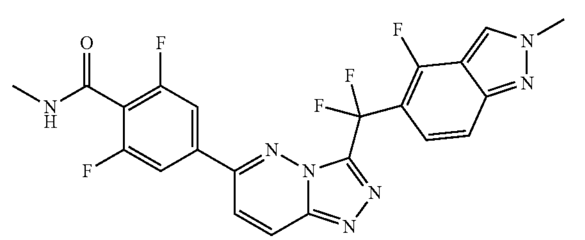 | 488.1 |
| 7 | B12 | 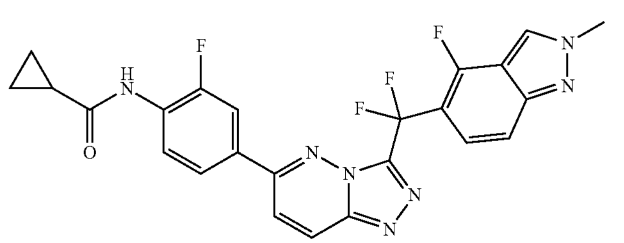 [SMILES: Cn1cc2c(F)c(C(F)(F)c3nnc4ccc(-c5ccc(NC(=O)C6CC6)c(F)c5)nn34)ccc2n1] | 496.2 |
| 8 | B14 | 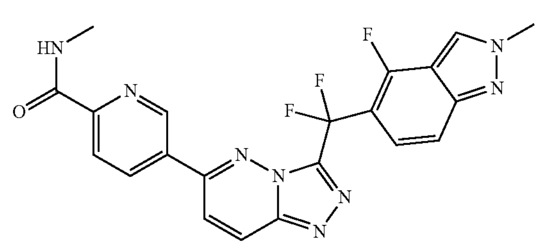 [SMILES: CNC(=O)c1ccc(-c2ccc3nnc(C(F)(F)c4ccc5nn(C)cc5c4F)n3n2)cn1] | 452.1 |

TABLE 1-continued

| | | Examples 1-17 | |
|---|---|---|---|
| Example | Intermediate | Structure | Molecular Ion [M + 1]+ |
| 9 | B16 | | 409.1 |
| 10 | B17 | | 413.1 |
| 11 | B18 | | 429.1 |
| 12 | B19 | | 443.1 |
| 13 | B20 | | 443.1 (M + Na) |

TABLE 1-continued
Examples 1-17
| Example | Intermediate | Structure | Molecular Ion [M + 1]+ |
|---|---|---|---|
| 14 | B23 | 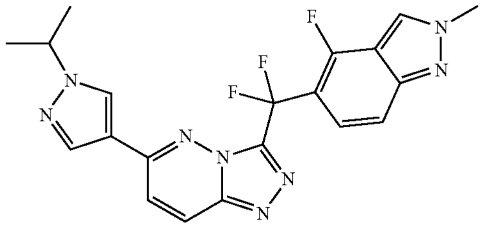 [SMILES: CC(C)n1cc(-c2ccc3nnc(C(F)(F)c4ccc5nn(C)cc5c4F)n3n2)cn1] | 427.2 |
| 15 | B25 | 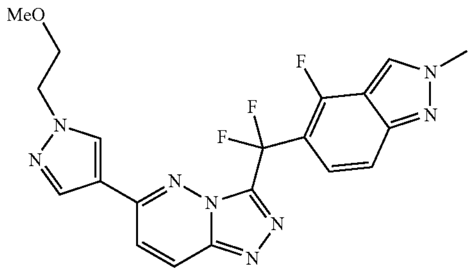 [SMILES: COCCn1cc(-c2ccc3nnc(C(F)(F)c4ccc5nn(C)cc5c4F)n3n2)cn1] | 443.2 |
| 16 | B26 | 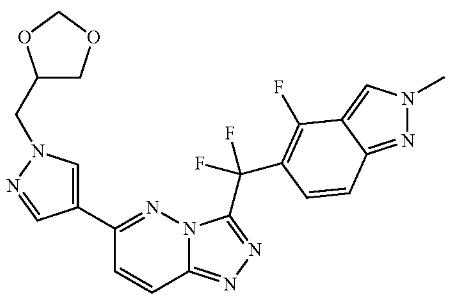 [SMILES: Cn1cc2c(F)c(C(F)(F)c3nnc4ccc(-c5cnn(CC6COCO6)c5)nn34)ccc2n1] | 471.2 |
| 17 | B27 | 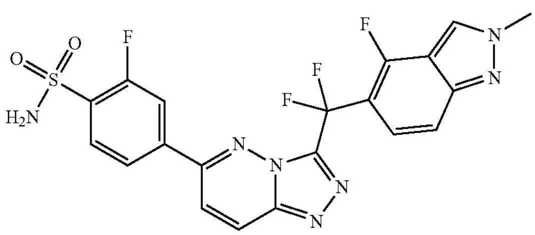 [SMILES: Cn1cc2c(F)c(C(F)(F)c3nnc4ccc(-c5ccc(S(N)(=O)=O)c(F)c5)nn34)ccc2n1] | 492.1 |
Example 44
6-(1-Cyclopropyl-1H-pyrazol-4-yl)-3-(difluoro(6-fluoro-2-methyl-(2H-indazol-5-yl)methyl-[1,2,4]triazolo[4,3-b]pyridazine
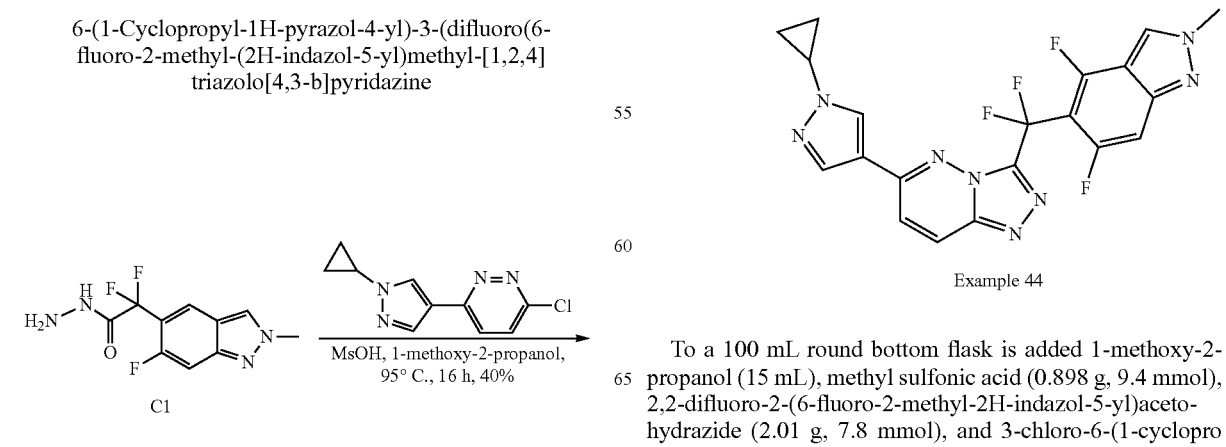
Example 44
To a 100 mL round bottom flask is added 1-methoxy-2-propanol (15 mL), methyl sulfonic acid (0.898 g, 9.4 mmol), 2,2-difluoro-2-(6-fluoro-2-methyl-2H-indazol-5-yl)acetohydrazide (2.01 g, 7.8 mmol), and 3-chloro-6-(1-cyclopro pyl-1H-pyrazol-4-yl) pyridazine (1.81 g, 8.2 mmol). The reaction mixture is stirred at 90° C. for 16 hr. After removal of solvent, the residue is purified on a silica gel flash chromatography with methanol/dichloromethane (1:20) to yield a light yellow solid (1.32 g, 40% yield). (MS: [M+1] 425)

Examples 18-52 are prepared from intermediates C1, C3-C5 by using the above methods (Table 2).

TABLE 2

Examples 18-52

| Example | Intermediate | Structure | Molecular Ion [M + 1]+ |
|---------|--------------|-----------|------------------------|
| 18 | B1 | 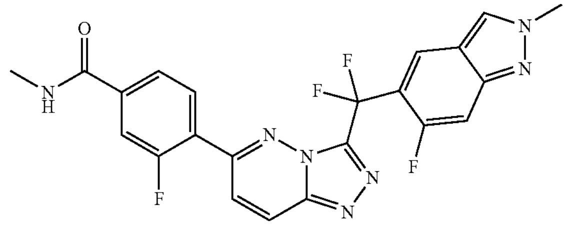 | 470.1 |
| 19 | B2 | 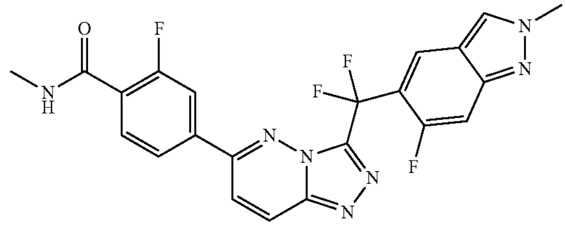 | 470.2 |
| 20 | B3 | 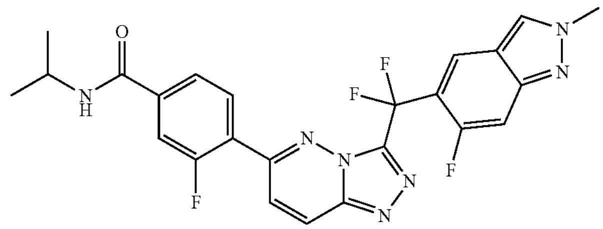 [SMILES: CC(C)NC(=O)c1ccc(-c2ccc3nnc(C(F)(F)c4cc5cn(C)nc5cc4F)n3n2)c(F)c1] | 498.2 |
| 21 | B4 | 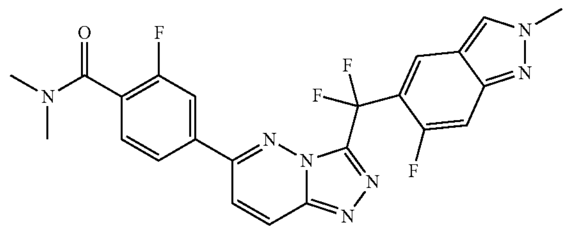 | 484.1 |
| 22 | B5 | 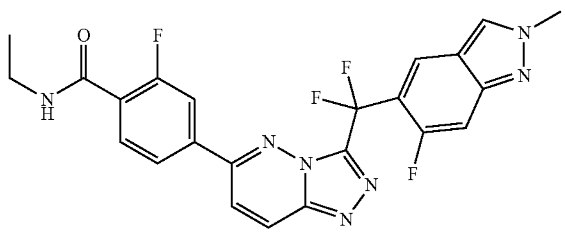 [SMILES: CCNC(=O)c1ccc(-c2ccc3nnc(C(F)(F)c4cc5cn(C)nc5cc4F)n3n2)cc1F] | 484.1 |
| 23 | B6 | 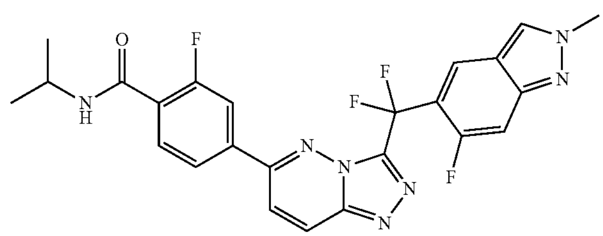 [SMILES: CC(C)NC(=O)c1ccc(-c2ccc3nnc(C(F)(F)c4cc5cn(C)nc5cc4F)n3n2)cc1F] | 498.2 |

TABLE 2-continued
Examples 18-52
| Example | Intermediate | Structure | Molecular Ion [M + 1]+ |
|---|---|---|---|
| 24 | B7 | 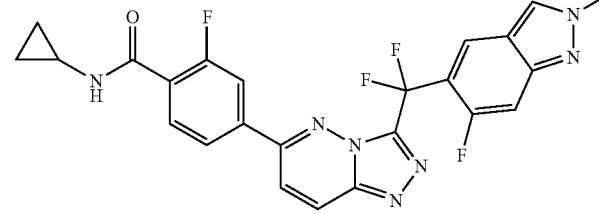 | 496.2 |
| 25 | B8 | 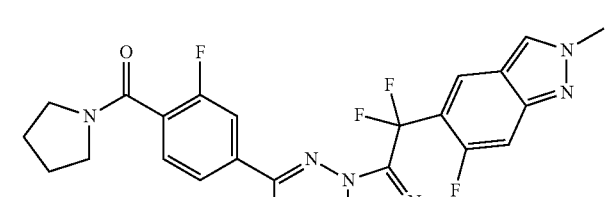 | 510.2 |
| 26 | B9 | 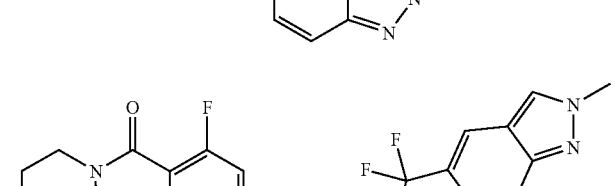 | 526.2 |
| 27 | B10 | 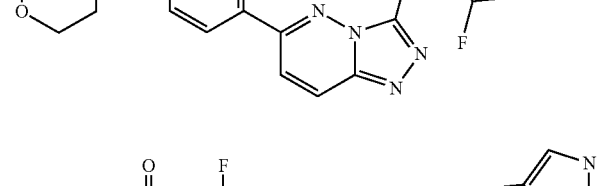 | 539.3 |
| 28 | B11 | 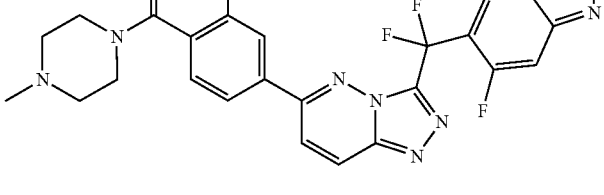 | 488.2 |
| 29 | B12 | 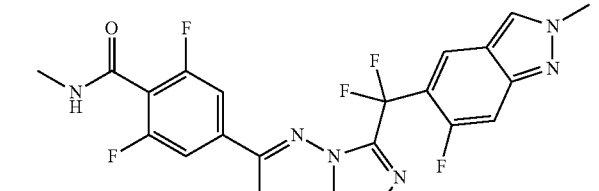 | 496.2 |

TABLE 2-continued

Examples 18-52

| Example | Intermediate | Structure | Molecular Ion [M + 1]+ |
|---------|--------------|-----------|------------------------|
| 30 | B13 | 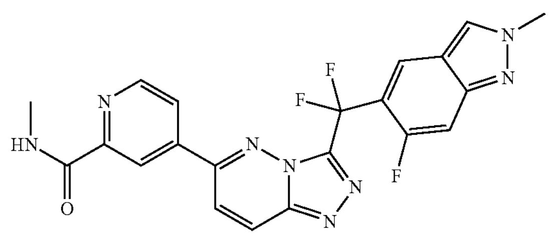 | 453.2 |
| 31 | B14 | 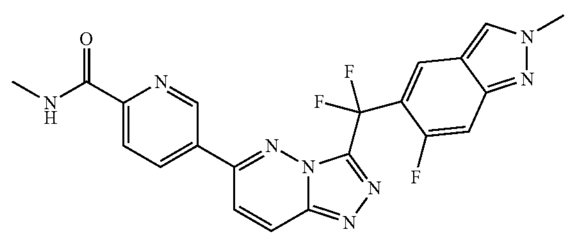 | 453.2 |
| 32 | B16 | 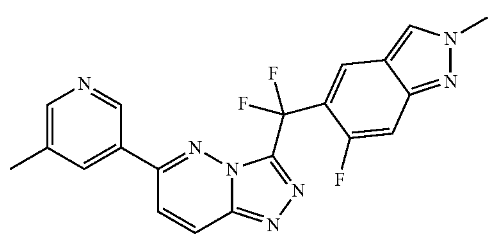 | 410.2 |
| 33 | B17 | 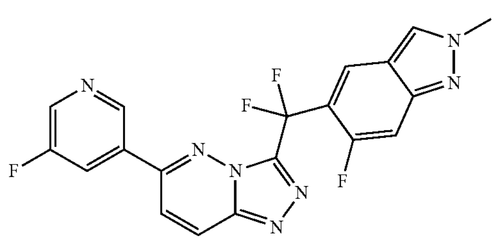 [SMILES: Cn1cc2cc(C(F)(F)c3nnc4ccc(-c5cncc(F)c5)nn34)c(F)cc2n1] | 414.2 |
| 34 | B18 | 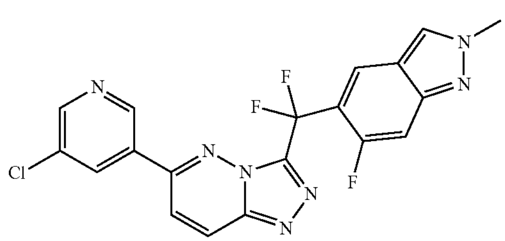 [SMILES: Cn1cc2cc(C(F)(F)c3nnc4ccc(-c5cncc(Cl)c5)nn34)c(F)cc2n1] | 430.2 |
| 35 | B20 | 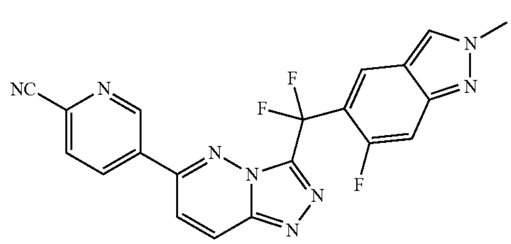 [SMILES: Cn1cc2cc(C(F)(F)c3nnc4ccc(-c5ccc(C#N)nc5)nn34)c(F)cc2n1] | 421.2 |

TABLE 2-continued

Examples 18-52

| Example | Intermediate | Structure | Molecular Ion [M + 1]+ |
|---------|--------------|-----------|------------------------|
| 36 | B21 | 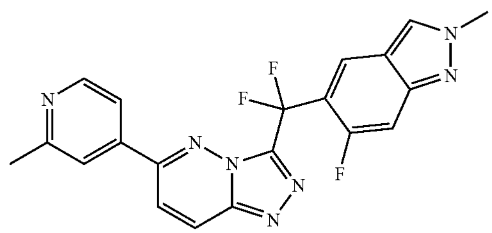 | 410.2 |
| 37 | B22 | 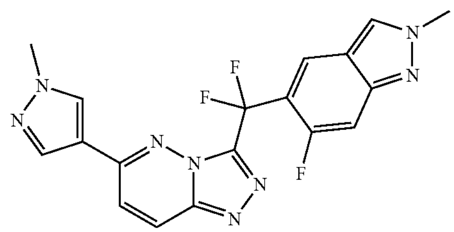 [SMILES: Cn1cc(-c2ccc3nnc(C(F)(F)c4cc5cn(C)nc5cc4F)n3n2)cn1] | 399.2 |
| 38 | B23 | 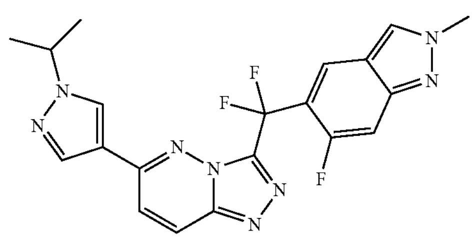 [SMILES: CC(C)n1cc(-c2ccc3nnc(C(F)(F)c4cc5cn(C)nc5cc4F)n3n2)cn1] | 427.2 |
| 39 | B24 | 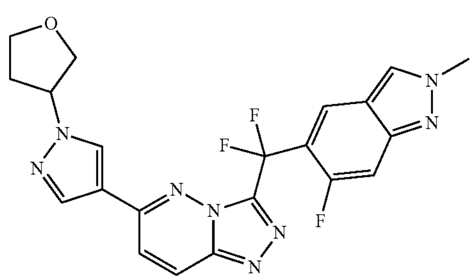 [SMILES: Cn1cc2cc(C(F)(F)c3nnc4ccc(-c5cnn(C6CCOC6)c5)nn34)c(F)cc2n1] | 455.2 |
| 40 | B25 | 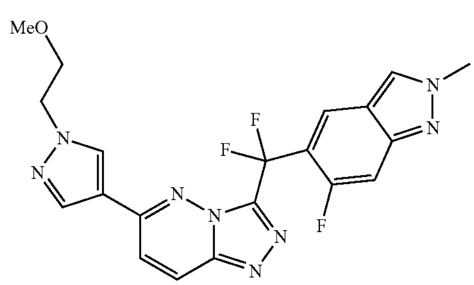 [SMILES: COCCn1cc(-c2ccc3nnc(C(F)(F)c4cc5cn(C)nc5cc4F)n3n2)cn1] | 443.2 |

TABLE 2-continued

Examples 18-52

| Example | Intermediate | Structure | Molecular Ion [M + 1]+ |
|---|---|---|---|
| 41 | B26 | 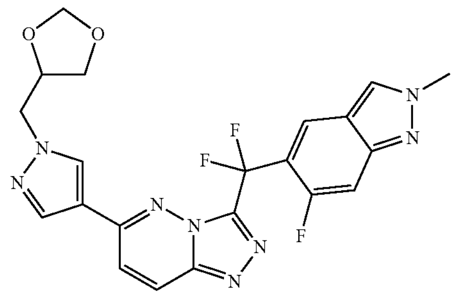 [SMILES: Cn1cc2cc(C(F)(F)c3nnc4ccc(-c5cnn(CC6COCO6)c5)nn34)c(F)cc2n1] | 471.2 |
| 42 | B28 | 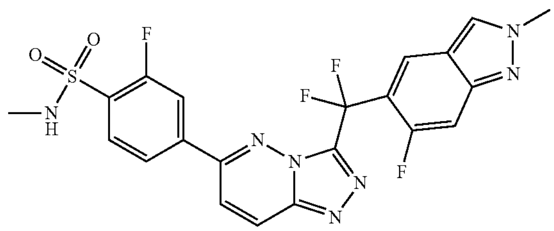 | 506.1 |
| 43 | B29 | 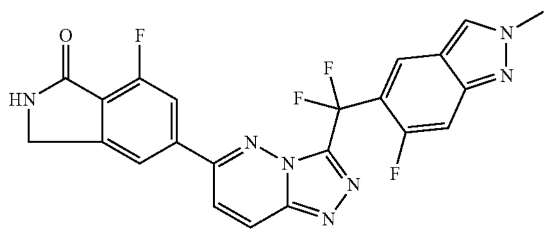 [SMILES: Cn1cc2cc(C(F)(F)c3nnc4ccc(-c5cc(F)c6c(c5)CNC6=O)nn34)c(F)cc2n1] | 468.2 |
| 44 | B30 | 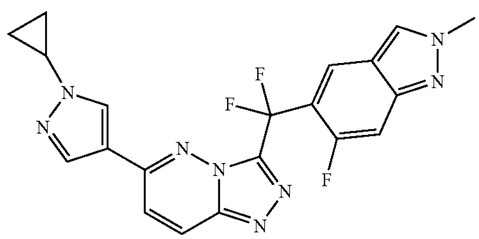 [SMILES: Cn1cc2cc(C(F)(F)c3nnc4ccc(-c5cnn(C6CC6)c5)nn34)c(F)cc2n1] | 425.1 |
| 45 | B31 | 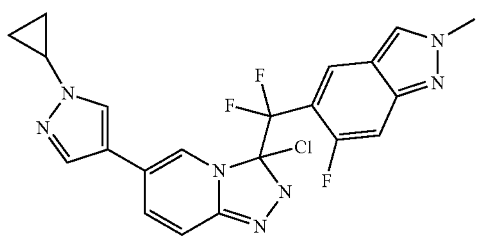 [SMILES: Cn1cc2cc(C(F)(F)C3(Cl)NN=C4C=CC(c5cnn(C6CC6)c5)=CN43)c(F)cc2n1] | 460.1 |
| 46 | B31 | 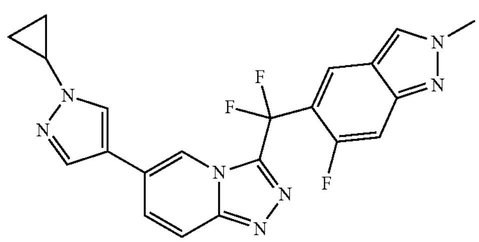 [SMILES: Cn1cc2cc(C(F)(F)c3nnc4ccc(-c5cnn(C6CC6)c5)cn34)c(F)cc2n1] | 424.1 |

TABLE 2-continued

Examples 18-52

| Example | Intermediate | Structure | Molecular Ion [M + 1]+ |
|---|---|---|---|
| 47 | B32 | 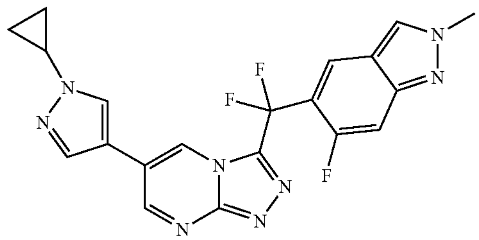 [SMILES: Cn1cc2cc(C(F)(F)c3nnc4ncc(-c5cnn(C6CC6)c5)cn34)c(F)cc2n1] | 425.0 |
| 48 | A31 | 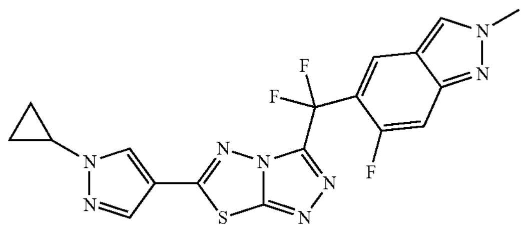 [SMILES: Cn1cc2cc(C(F)(F)c3nnc4sc(-c5cnn(C6CC6)c5)nn34)c(F)cc2n1] | ND |
| 49 | C5 | 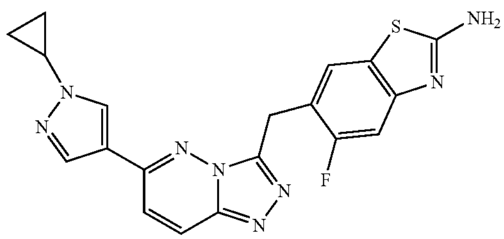 [SMILES: Nc1nc2cc(F)c(Cc3nnc4ccc(-c5cnn(C6CC6)c5)nn34)cc2s1] | 407.1 |
| 50 | C3 | 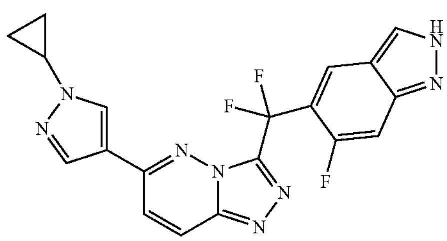 [SMILES: Fc1cc2n[nH]cc2cc1C(F)(F)c1nnc2ccc(-c3cnn(C4CC4)c3)nn12] | 411.1 |
| 51 | C3 | 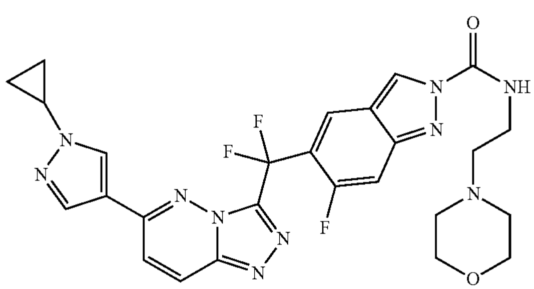 [SMILES: O=C(NCCN1CCOCC1)n1cc2cc(C(F)(F)c3nnc4ccc(-c5cnn(C6CC6)c5)nn34)c(F)cc2n1] | 567.1 |
| 52 | C4 | 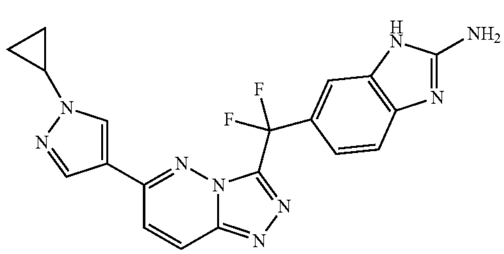 [SMILES: Nc1nc2ccc(C(F)(F)c3nnc4ccc(-c5cnn(C6CC6)c5)nn34)cc2[nH]1] | 408.1 |

Examples on Biological Activities

Biological Activity Example 1 c-Met In Vitro Kinase Assay

[Method] Use Lance@Ultra Ulight™-TK test kits from PerKinElmer to evaluate the inhibition of c-Met kinase by the compounds

[Instrument] ENVISION plate reader of PerKinElmer

[Materials] Optiplate-384 well plate (PerKinElmer), kinase buffer (50 mM Hepes pH7.5, 25 mM NaCl, 2 mM DTT, 0.01% Tween 20, 5 mM $Mg^{2+}$, 0.5 mM $Mn^{2+}$), c-Met kinase (1038-1346AA, prepared in-house), c-Met substrate (PerKinElmer, #TRF0127-M), Lance@Eu-W 1024-anti-phosphotyrosine (PT66), (PerKinElmer, #AD0068), ATP (Invitrogen), DMSO (Sigma, #34869), water (Millipore, model Milli-Q).

[Procedure] A mixture of c-Met kinase (final concentration 12.5 nM) and test compound (final DMSO is 0.5%) is pre-incubated at 30° C. for 20 min. Then ATP (final concentration 2.5 uM) and kinase substrate (final concentration 50 nM) are added. The resulting mixture is kept at 30° C. for 1 hr, followed by addition of the c-Met antibody. After 1 hr, the plate is read at 615 nm and 665 nm. The ratio of absorption values at 665 nm and 615 nm is calculated and used for the data analysis as follows. This assay has a Minimum Significant Ratio (MSA) of 2-3.

[Samples] All exampled compounds and Crizotinib as the positive control

[Data Analysis] Background—the ratio of 665 nm/615 nm (no enzyme):0.003285

Max—the ratio of 665 nm/615 nm (no test compound): 0.075356

$$\text{Inhibition (\%): } 100 \times \frac{\text{Max-Test}}{\text{Max-Background}}$$

[Software] Use CBIS data analysis software to calculate $IC_{50}$ values

Biological Activity Example 2

S114 Cell-Based ELISA

[Method] Use ELISA to measure the phosphorylation of c-Met protein in S114 cells

[Instrument] ENVISION plate reader of PerKinElmer

[Materials] S114 cell (NIH), 96 well plate (CORNING #3596), DMEM culture medium (Gibco, #11965-092), 96 well plate (Thermo, #14-245-61), PBS (Invitrogen, #10010023), fetal bovine serum (Gibco, #16000044), Fibronectin (Invitrogen, #33016-015), 1/2Tris ammonium bicarbonate (25 mM Tris, 100 mM NaCl, 12 mM $NH_4HCO_3$, pH 7.5), blocking buffer (25 mM Hepes, 100 mM NaCl, 0.2% Tween20, pH 7.5), binding buffer (0.3% gelatin, 25 mM Hepes, 100 mM NaCl, 0.01% Tween20, pH 7.5), lysis buffer (50 mM Tris, 150 mM NaCl, 1.25% CHAPS, 1 piece of protease inhibitor/10 ml, 1 piece of phosphatase inhibitor/10 mL), DMSO (Sigma, #D2650); capture antibody (anti-c-Met antibody, Cell Signaling, #3148s), 1st antibody (anti-phosphorylation c-Met antibody, R&D Systems, #AF2480), 2nd antibody (Anti-rabbit IgG HRP-linked antibody, Cell Signaling, #7074), A.B.T.S (Sigma, #A1888), A.B.T.S solution (0.1% A.B.T.S, 0.1 mM citric acid, 0.1 mM disodium phosphate), 30% hydroperoxide (Sinopharm), pure water (Millipore, model Milli-Q).

[Procedure] S114 cells are cultured in DMEM medium (containing 10% FBS). When cells reach 80% confluency, they are collected by trypsinization and centrifugation at 800 rpm for 5 min. The cells are re-suspended in DMEM and adjusted to a density of 500,000 cells/mL. A 96-well plate is pretreated with a solution of Firbronectin in PBS (5 μg/mL) at 100 μL per well for 2 hr. The cell suspension is split into the 96-well culture plate at 100 uL per well and incubated (37° C., 5% $CO_2$) overnight. The capture antibody is diluted with 1/2 Tris-ammonium bicarbonate buffer (1:1000) and transferred into a 96-well absorption plate (70 μL per well) at 4° C. overnight. The solution is discarded and the plate is washed with blocking buffer, followed by adding blocking buffer (150 μL per well), and kept at room temperature for 1 hr. The medium in the 96-well culture plate is discarded and the plate is washed with DMEM (without FBS). Then 80 μL of DMEM (without FBS) and 20 μL of test compound solution at various concentrations in DMEM (without FBS) are added. The culture plate is kept in a culture incubator for 30 min (37° C., 5% $CO_2$). The cell culture medium is discarded and the culture plate is washed with PBS, followed by adding lysis buffer (50 μL per well) and incubated at 4° C. for 20 min. The solution in the absorption plate is discarded and the plate is washed with binding buffer. To each well of the absorption plate is added binding buffer (50 μL) and lysate (40 μL) from the above culture plate; then the plate is incubated at room temperature for 2 hours. The culture medium is discarded and the plate is washed twice with binding buffer, followed by adding a solution of 1st antibody (diluted with binding buffer 1:1000, 100 μL per well) and incubated at 37° C. for 1 hr. The solution is discarded and the plate is washed twice with binding buffer. Then a solution of 2nd antibody is added (100 μL per well) and incubated at 37° C. for another hour. The medium is discarded and the plate is washed twice with binding buffer and once with PBS. To each well, 100 μL of A.B.T.S solution is added and incubated at 37° C. for 30 min. Then OD405 is analyzed on an ENVISION plate reader. This assay has a Minimum Significant Ratio (MSA) of 2-3.

[Samples] All exemplified compounds and Crizotinib as the positive control

[Data Analysis] Background (no cell lysate): 0.084

Max (no test compound): 0.517

$$\text{Inhibition (\%): } 100 \times \frac{\text{Max-Test}}{\text{Max-Background}}$$

[Software] Use CBIS data analysis software to calculate $IC_{50}$ values

TABLE 3

Biology Activity of Compounds 1-52 (IC50, nM)

| Example | c-Met Enzyme | S114 Cell |
|---|---|---|
| 1 | 48.8 | 3.9 |
| 2 | 148.0 | 103.0 |
| 3 | 69.3 | 71.5 |
| 4 | 83.9 | 2.6 |
| 5 | 45.4 | 23.2 |
| 6 | 36.5 | 9.5 |
| 7 | 76.4 | 49.6 |
| 8 | 149.0 | 122.0 |

TABLE 3-continued

Biology Activity of Compounds 1-52 (IC50, nM)

| Example | c-Met Enzyme | S114 Cell |
|---|---|---|
| 9 | 119.0 | 85.0 |
| 10 | 261.0 | 142.0 |
| 11 | 194.0 | 42.0 |
| 12 | 158.0 | 96.6 |
| 13 | 182.0 | 190.0 |
| 14 | 102.0 | 22.5 |
| 15 | 380.0 | 383.0 |
| 16 | 247.0 | 179.0 |
| 17 | 77.6 | 55.6 |
| 18 | 90.8 | 206.2 |
| 19 | 25.6 | 5.7 |
| 20 | 137.4 | 157.6 |
| 21 | 180.0 | 262.0 |
| 22 | 20.7 | 15.5 |
| 23 | 41.6 | 1.1 |
| 24 | 43.4 | 14.9 |
| 25 | 125.0 | 52.7 |
| 26 | 357.0 | 299.0 |
| 27 | 148.0 | 324.0 |
| 28 | 27.7 | 14.2 |
| 29 | 29.5 | 7.9 |
| 30 | 51.8 | 45.0 |
| 31 | 81.4 | 60.6 |
| 32 | 109.0 | 37.7 |
| 33 | 242.0 | 210.0 |
| 34 | 53.2 | 57.6 |
| 35 | 65.0 | 88.1 |
| 36 | 113.0 | 34.0 |
| 37 | 50.7 | 13.7 |
| 38 | 82.9 | 44.1 |
| 39 | 79.7 | 204.0 |
| 40 | 203.0 | 134.0 |
| 41 | 127.0 | 348.0 |
| 42 | 136.0 | 406.0 |
| 43 | 23.3 | 35.2 |
| 44 | 31.6 | 7.8 |
| 45 | 274.0 | 270.0 |
| 46 | 159.0 | 139.0 |
| 47 | 38.0 | 22.0 |
| 48 | ND | ND |
| 49 | 38.0 | 65.0 |
| 50 | 1435 | 527.0 |
| 51 | 4129 | |
| 52 | 568.0 | |

We claim:
1. A compound of Formula I

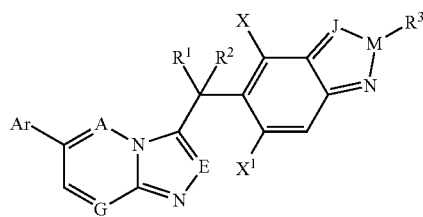

wherein:
$R^1$ and $R^2$ are independently hydrogen or halogen;
X and $X^1$ are independently hydrogen or halogen;
A is N;
G is CH;
E is N;
J is CH or N;
M is N or C;
Ar is aryl or heteroaryl, optionally substituted with 1-3 substituents independent selected from: $C_{1-6}$alkyl, $C_{1-6}$alkoxyl, halo$C_{1-6}$alkyl, halo$C_{1-6}$ alkoxy, $C_{3-7}$cycloalkyl, halogen, cyano, amino, —CONR$^4$R$^5$, —NHCOR$^6$, —SO$_2$NR$^7$R$^6$, amino-$C_{1-6}$alkyl-, heterocyclyl and heterocyclyl-$C_{1-6}$alkyl-, or two connected substituents together with the atoms to which they are attached form a 4-6 membered lactam fused with the aryl or heteroaryl;
$R^3$ is hydrogen, $C_{1-6}$alkyl, $C_{1-6}$alkoxy, halo$C_{1-6}$alkyl, halogen, amino, or —CONH—$C_{1-6}$alkyl-heterocyclyl;
$R^4$ and $R^5$ are independently hydrogen, $C_{1-6}$alkyl, $C_{3-7}$cycloalkyl, heterocyclyl-$C_{1-6}$alkyl, or $R^4$ and $R^5$ together with the N to which they are attached form a heterocyclyl;
$R^6$ is $C_{1-6}$alkyl or $C_{3-7}$cycloalkyl; and
$R^7$ and $R^8$ are independently hydrogen or $C_{1-6}$alkyl;
or a pharmaceutically acceptable salt thereof.

2. The compound of claim 1, or a pharmaceutically acceptable salt thereof, wherein heterocyclyl, alone or in the terms heterocyclyl-$C_{1-6}$alkyl or —CONH—$C_{1-6}$alkl-heterocyclyl, is piperidinyl, piperazinyl, homopiperazinyl, azepinyl, dioxolanyl, pyrrolidinyl, pyrazolidinyl, imidazolidinyl, imidazolinyl, pyridinyl, pyridazinyl, pyrimidinyl, oxazolidinyl, isoxazolyl, morpholinyl, thiazolidinyl, isothiazolyl, quinuclidinyl, thiadiazolyl, dihydrofuryl, tetrahydrofuranyl, dihydropyranyl, tetrahydropyranyl, thiomorpholinyl, thiomorpholinylsulfoxide, or thiomorpholinylsulfone.

3. The compound of claim 1, or a pharmaceutically acceptable salt thereof, wherein $R^1$ and $R^2$ are F.

4. The compound according to claim 1, or a pharmaceutically acceptable salt thereof, wherein one of X and $X^1$ is F while the other is hydrogen.

5. The compound according to claim 1, or a pharmaceutically acceptable salt thereof, wherein $R^3$ is $C_{1-6}$alkyl.

6. The compound of claim 5, or a pharmaceutically acceptable salt thereof, wherein $R^3$ is methyl.

7. The compound according to claim 1, or a pharmaceutically acceptable salt thereof, wherein Ar is aryl or heteroaryl, optionally substituted with 1-3 substituents independent selected from: $C_{1-6}$alky, $C_{3-7}$cycloalkyl, halogen, cyano, —CONR$^4$R$^5$, —NHCOR$^6$, —SO$_2$NR$^7$R$^8$, $C_{1-6}$alkoxyl-$C_{1-6}$alkyl-, heterocyclyl, and heterocyclyl-$C_{1-6}$alkyl-.

8. The compound of claim 7, or a pharmaceutically acceptable salt thereof, wherein Ar is phenyl optionally substituted with 1-3 substituents independently selected from: $C_{1-6}$alky, $C_{3-7}$cycloalkyl, halogen, cyano, —CONR$^4$R$^5$, —NHCOR$^6$, —SO$_2$NR$^7$R$^6$, $C_{1-6}$alkoxyl-$C_{1-6}$alkyl-, heterocyclyl, and heterocyclyl-$C_{1-6}$alkyl-.

9. The compound of claim 8, or a pharmaceutically acceptable salt thereof, wherein the phenyl is disubstituted with F and —CONR$^4$R$^5$.

10. The compound of claim 9, or a pharmaceutically acceptable salt thereof, wherein F is meta to the point of attachment and —CONR$^4$R$^5$ para to the point of attachment.

11. The compound of claim 9, or a pharmaceutically acceptable salt thereof, wherein $R^4$ and $R^5$ are independently hydrogen, $C_{1-6}$alky, or $C_{3-7}$cycloalkyl.

12. The compound of claim 9, or a pharmaceutically acceptable salt thereof, wherein $R^4$ and $R^5$ together with the N to which they are attached form a heterocyclyl.

13. The compound of claim 12, or a pharmaceutically acceptable salt thereof, wherein the heterocyclyl is pyrrolidinyl, morpholinyl or methylpiperazinyl.

14. The compound of claim 7, or a pharmaceutically acceptable salt thereof, wherein Ar is heteroaryl selected from furyl, pyridyl, pyridazinyl, pyrimidinyl, pyrazinyl, thiazolyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, isoindolyl, thiazolyl, benzothiazolyl, isothiazolyl, benzoxazolyl, benzisoxazolyloxazolyl, and quinolyl, optionally substituted with 1-3 substituents independent selected from: $C_{1-6}$alkyl, $C_{3-7}$cycloalkyl, halogen, cyano, —CONR$^4$R$^5$, —NHCOR$^6$, —SO$_2$NR$^7$R$^8$, $C_{1-6}$ alkoxyl-$C_{1-6}$alkyl-, heterocyclyl, and heterocyclyl-$C_{1-6}$alkyl-.

15. The compound of claim 14, or a pharmaceutically acceptable salt thereof, wherein the heteroaryl is pyridyl, optionally substituted with 1-3 substituents independent selected from: $C_{1-6}$alkyl, $C_{3-7}$cycloalky, halogen, cyano, —CONR$^4$R$^5$, —NHCOR$^6$, —SO$_2$NR$^7$R$^8$, $C_{1-6}$ alkoxyl-$C_{1-6}$alkyl-, heterocyclyl, and heterocyclyl-$C_{1-6}$alkyl-.

16. The compound of claim 15, or a pharmaceutically acceptable salt thereof, wherein the pyridyl is monosubstituted with $C_{1-6}$alkyl, halogen, cyano, or —CONR$^4$R$^5$.

17. The compound of claim 16, or a pharmaceutically acceptable salt thereof, wherein R$^4$ and R$^5$ are independently hydrogen, $C_{1-6}$alky, or $C_{3-7}$cycloalkyl.

18. The compound of claim 16, or a pharmaceutically acceptable salt thereof, wherein the pyridyl is monosubstituted with $C_{1-6}$alkyl, halogen, or cyano.

19. The compound according to claim 16, or a pharmaceutically acceptable salt thereof, wherein the pyridyl ring N is meta to the point of attachment.

20. The compound of claim 14, or a pharmaceutically acceptable salt thereof, wherein the heteroaryl is pyrazolyl, optionally substituted with 1-3 substituents independent selected from: $C_{1-6}$alkyl, $C_{3-7}$cycloalkyl, halogen, cyano, —CONR$^4$R$^5$, —NHCOR$^6$, —SO$_2$NR$^7$R$^5$, $C_{1-6}$ alkoxy-$C_{1-6}$alkyl-, heterocyclyl, and heterocyclyl-$C_{1-6}$alkyl-.

21. The compound of claim 20, or a pharmaceutically acceptable salt thereof, wherein the pyrazolyl is monosubstituted with $C_{1-6}$alkyl, $C_{3-7}$cycloalky, $C_{1-6}$alkoxy-$C_{1-6}$alkyl-, heterocyclyl, or heterocyclyl-$C_{1-6}$alkyl-.

22. The compound of claim 21, or a pharmaceutically acceptable salt thereof, wherein the pyrazolyl is monosubstituted with $C_{1-6}$alkyl, $C_{3-7}$cycloalky, or $C_{1-6}$alkoxy-$C_{1-6}$alkyl-.

23. The compound of claim 22, or a pharmaceutically acceptable salt thereof, wherein the pyrazolyl is monosubstituted with $C_{3-7}$cycloalky.

24. The compound of claim 23, or a pharmaceutically acceptable salt thereof, wherein the pyrazolyl is monosubstituted with cyclopropyl.

25. The compound according to claim 21, or a pharmaceutically acceptable salt thereof, wherein the pyrazolyl is attached at the 4-position and substituted at the 1-position.

26. The compound according to claim 1, or a pharmaceutically acceptable salt thereof, wherein J is CH.

27. The compound according to claim 1, or a pharmaceutically acceptable salt thereof, wherein M is N.

28. The compound according to claim 1, or a pharmaceutically acceptable salt thereof, which is selected from the group consisted of:

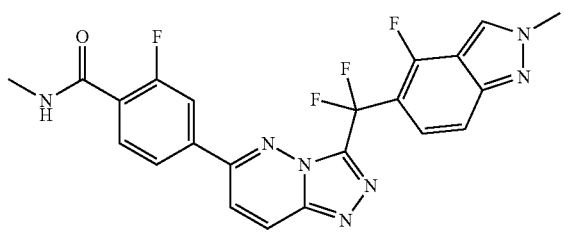

-continued

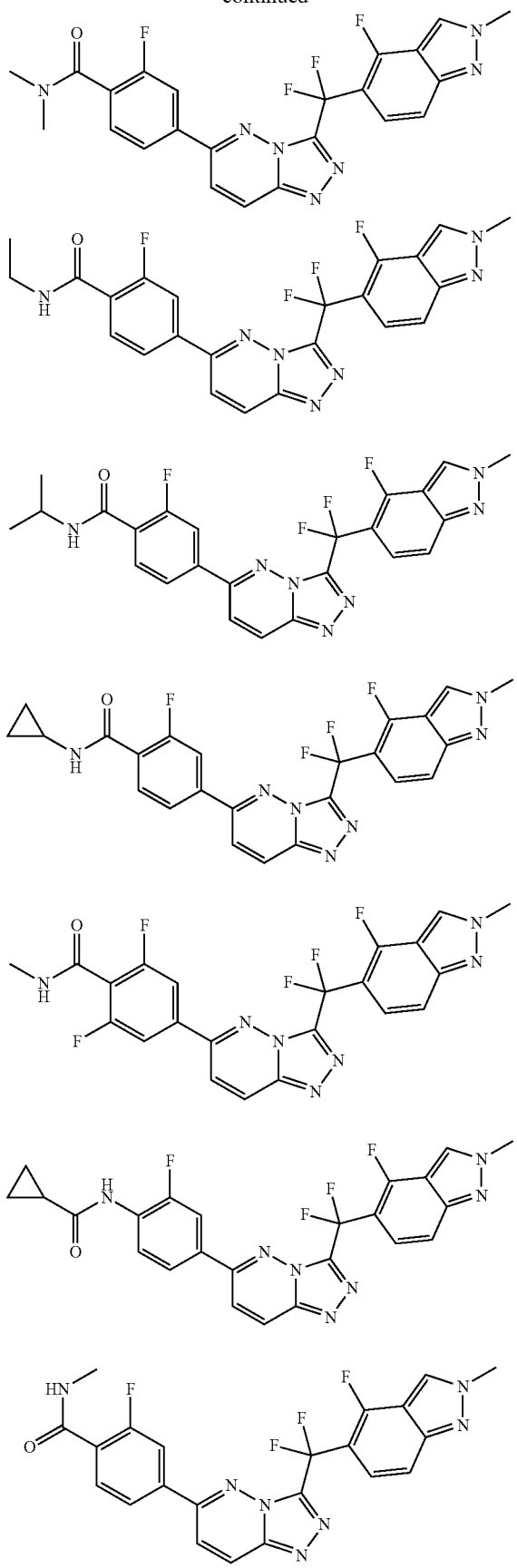

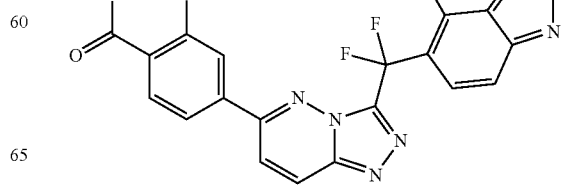

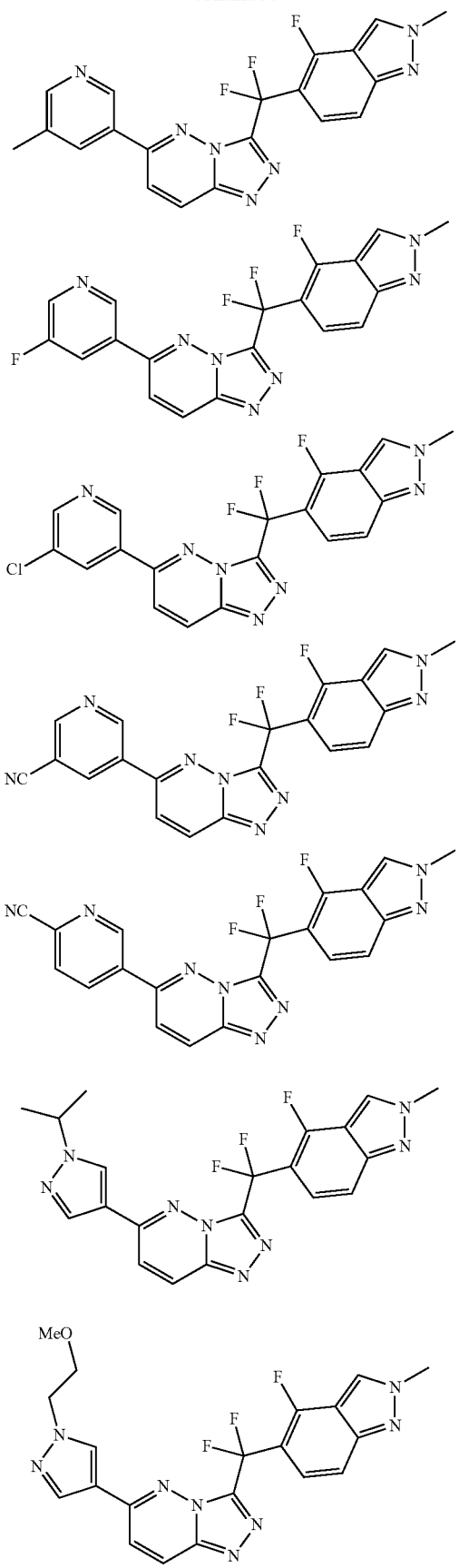
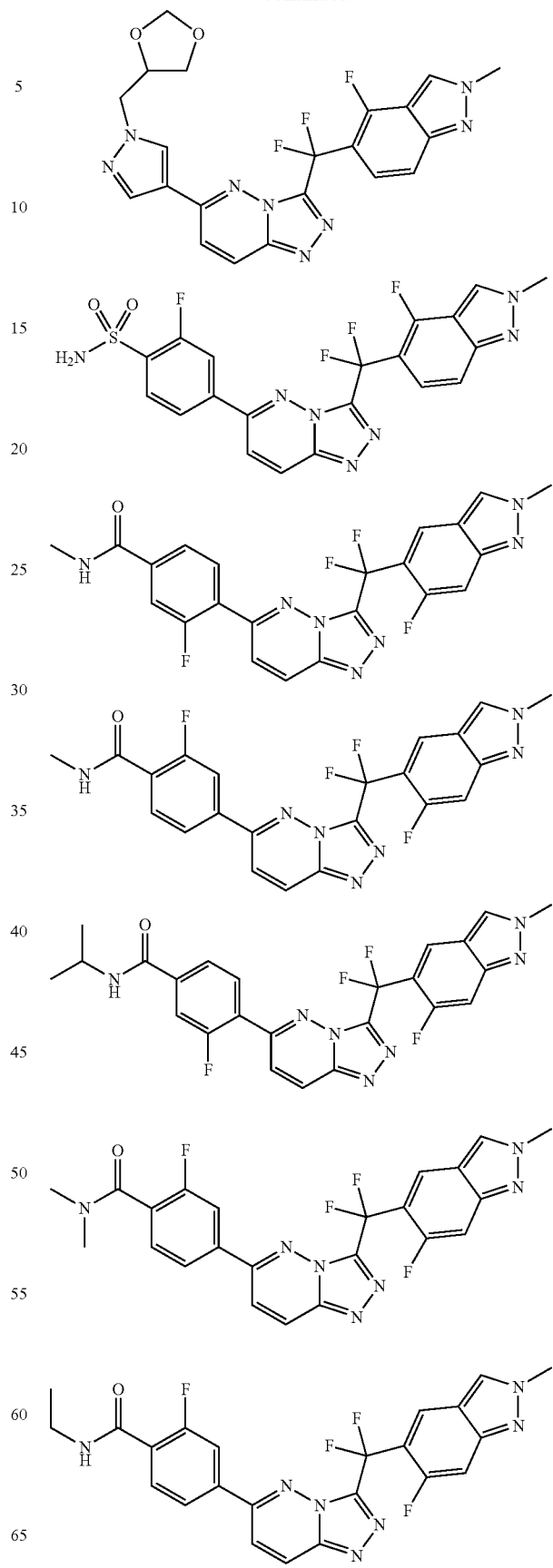

67
-continued
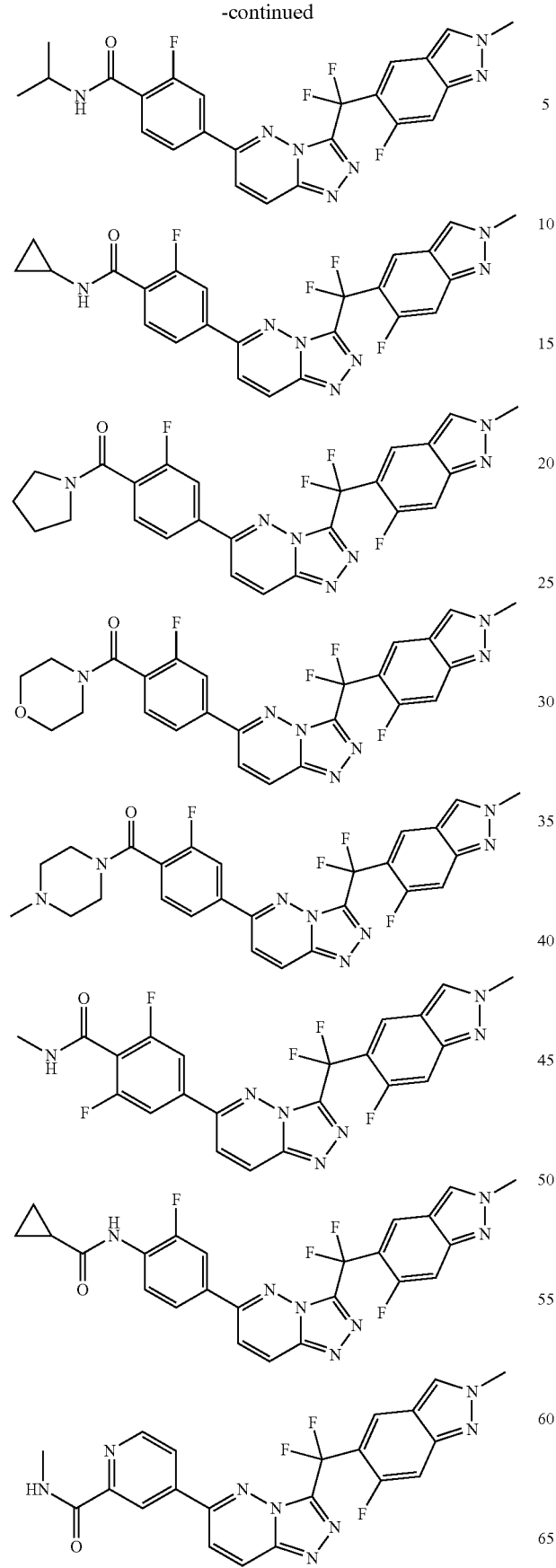
68
-continued
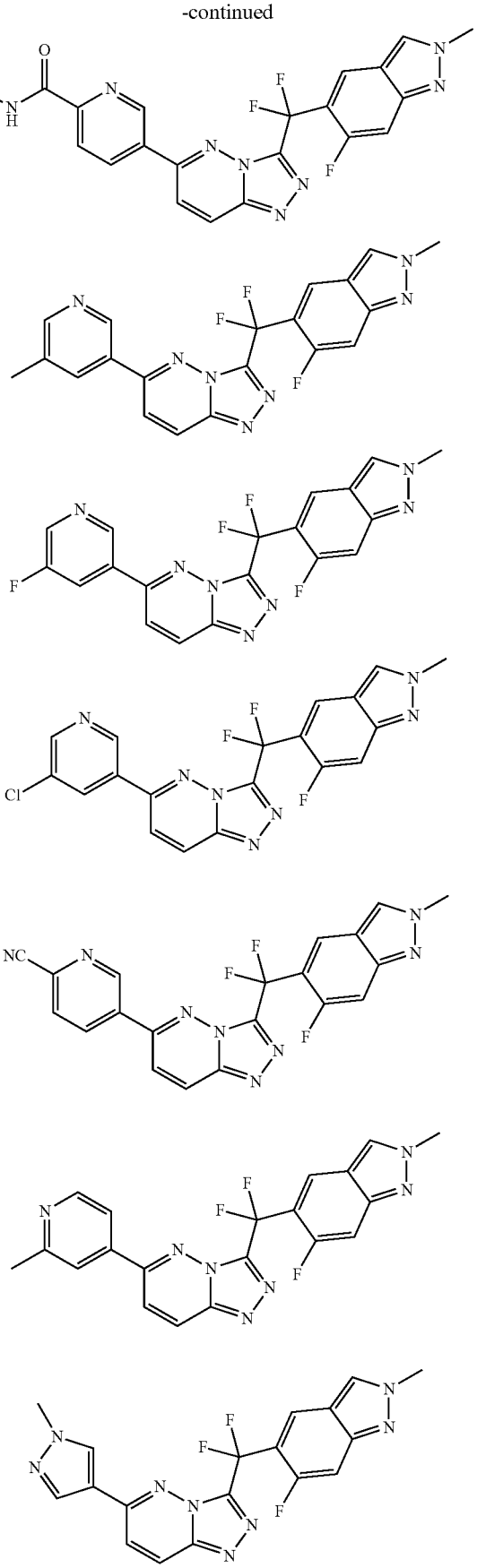

69
-continued
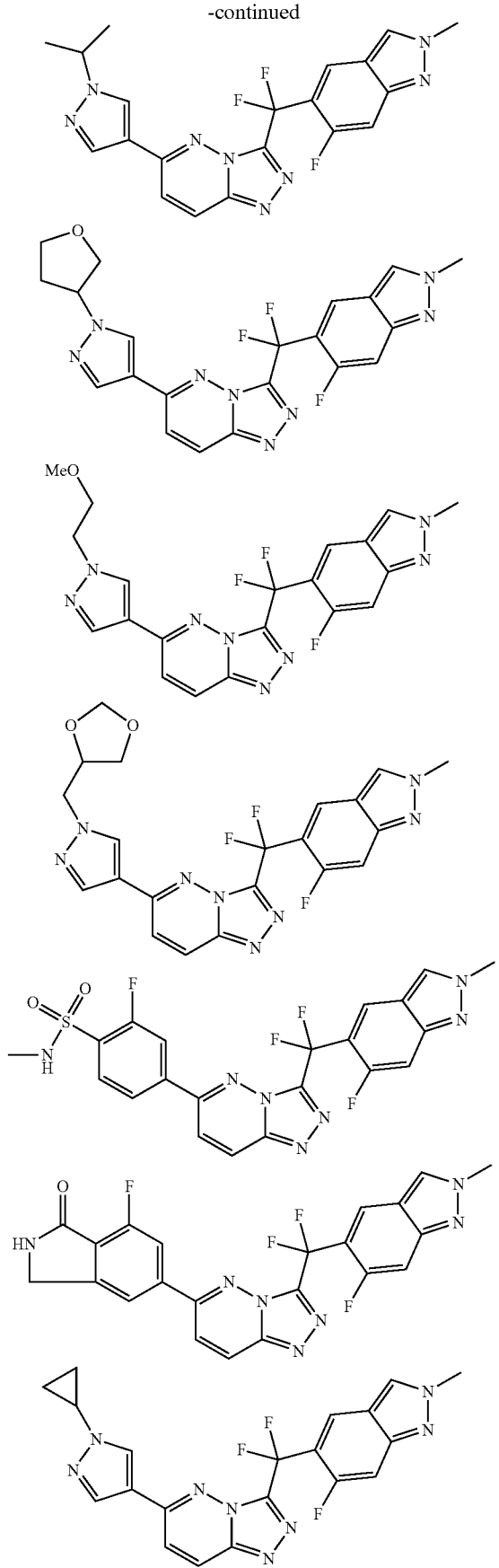
70
-continued
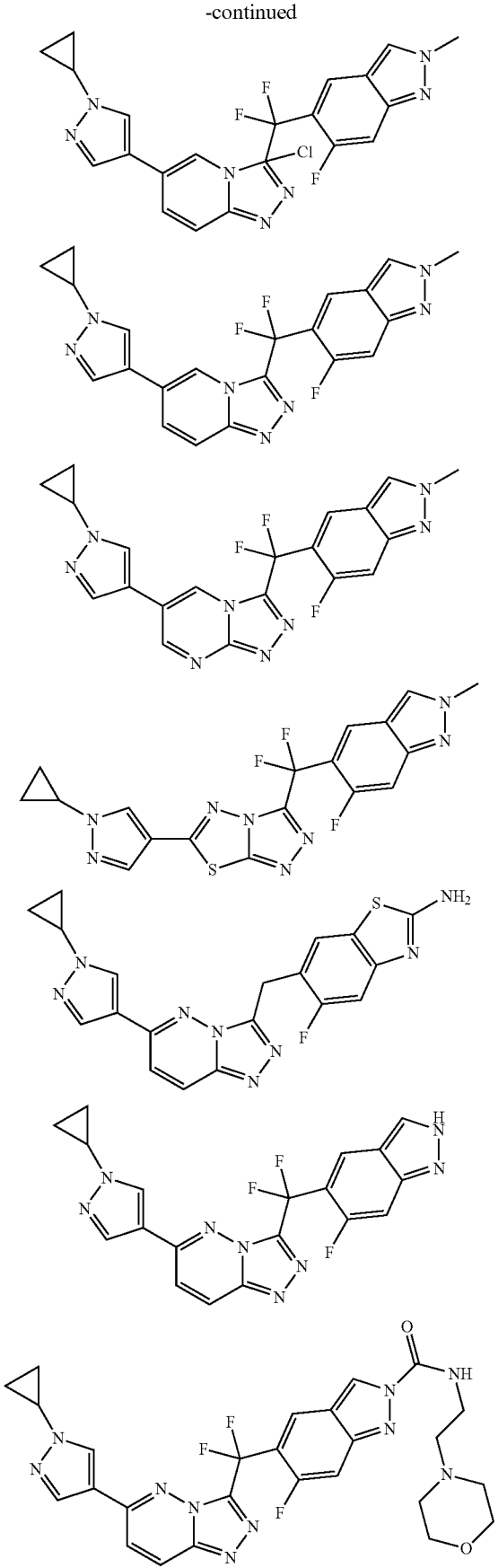

-continued

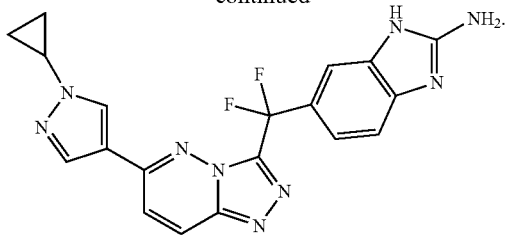

29. A pharmaceutical composition comprising a compound according to any one of claims 1-28, or a pharmaceutically acceptable salt thereof, together with a pharmaceutically acceptable carrier or excipient.

30. A compound according to any one of claims 1-28, or a pharmaceutically acceptable salt thereof, for use as a medicament.

31. A compound according to any one of claims 1-28, or a pharmaceutically acceptable salt thereof, for in the treatment of cancer.

32. A method of treating cancer comprising administering to a mammal in need of such treatment a therapeutically effective amount of a compound according to any one of claims 1-28, or a pharmaceutically acceptable salt thereof.

33. The method of claim 32, wherein cancer is colorectal, breast, liver, lung, prostate cancer, pancreatic cancer, stomach cancer, bladder cancer, ovarian cancer, melanoma, neuroblastoma, cervical kidney cancer or kidney cancer, leukemia or lymphoma.

34. The method of claim 33, wherein cancer is breast, colon, liver, lung, prostate cancer, or a gastrointestinal stromal tumor.

35. The method of claim 32, wherein cancer is myeloid leukemia and acute lymphocytic leukemia, and pancreatic cancer.

* * * * *